(12) United States Patent
Frater et al.

(10) Patent No.: US 11,071,838 B2
(45) Date of Patent: Jul. 27, 2021

(54) MASK VENT WITH SIDE WALL

(71) Applicant: ResMed Pty Ltd, Bella Vista (AU)

(72) Inventors: Robert Henry Frater, Sydney (AU); Quangang Yang, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 699 days.

(21) Appl. No.: 15/023,917

(22) PCT Filed: Sep. 30, 2014

(86) PCT No.: PCT/AU2014/050257
§ 371 (c)(1),
(2) Date: Mar. 22, 2016

(87) PCT Pub. No.: WO2015/048849
PCT Pub. Date: Apr. 9, 2015

(65) Prior Publication Data
US 2016/0271351 A1 Sep. 22, 2016

(30) Foreign Application Priority Data

Oct. 3, 2013 (AU) .................................. 2013903819

(51) Int. Cl.
*A61M 16/06* (2006.01)
*A61M 16/08* (2006.01)
(Continued)

(52) U.S. Cl.
CPC .... *A61M 16/0622* (2014.02); *A61M 16/0057* (2013.01); *A61M 16/06* (2013.01);
(Continued)

(58) Field of Classification Search
CPC .......... A61M 16/0622; A61M 16/0666; A61M 16/0683; A61M 16/06; A61M 16/065;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| EP | 1 582 230 B1 | 5/2008 |
| EP | 2 022 528 A2 | 2/2009 |

(Continued)

OTHER PUBLICATIONS

"*Respiratory Physiology*", by John B. West, Lippincott Williams & Wilkins, 9th edition published 2012 (8 pages).

(Continued)

*Primary Examiner* — Tu A Vo
*Assistant Examiner* — Alexander Morales
(74) *Attorney, Agent, or Firm* — Nixon & Vanderhye P.C.

(57) ABSTRACT

A vent arrangement for a mask system includes a mask component and a mask vent provided to the mask component. The mask vent includes a plurality of vent holes each extending through a thickness of the mask component and each including a vent exit, and a continuous side wall structured to surround the plurality of vent exits of the vent holes.

27 Claims, 34 Drawing Sheets

(51) Int. Cl.
*A61M 16/00* (2006.01)
*A61M 16/16* (2006.01)
*A61M 16/20* (2006.01)
*A61M 16/10* (2006.01)
*F24F 7/00* (2021.01)

(52) U.S. Cl.
CPC ..... *A61M 16/0816* (2013.01); *A61M 16/0066* (2013.01); *A61M 16/065* (2014.02); *A61M 16/0666* (2013.01); *A61M 16/0683* (2013.01); *A61M 16/107* (2014.02); *A61M 16/16* (2013.01); *A61M 16/208* (2013.01); *A61M 2202/0225* (2013.01); *A61M 2205/42* (2013.01); *F24F 2007/0025* (2021.01)

(58) Field of Classification Search
CPC ............ A61M 16/066; A61M 16/0057; A61M 16/0816; A61M 16/16; A61M 16/107; A61M 16/208; A61M 2202/0225; A61M 2205/42; F01N 1/08; F01N 2340/00
USPC .......................... 128/200.18, 201.17, 206.16
See application file for complete search history.

(56) References Cited

U.S. PATENT DOCUMENTS

| | | | |
|---|---|---|---|
| 6,532,959 B1 | 3/2003 | Berthon-Jones | |
| 6,581,594 B1 | 6/2003 | Drew et al. | |
| 6,907,882 B2 | 6/2005 | Ging et al. | |
| 7,159,587 B2 * | 1/2007 | Drew | A61M 16/06 128/204.18 |
| 7,207,335 B2 * | 4/2007 | Kwok | A61M 16/06 128/205.24 |
| 7,523,754 B2 | 4/2009 | Lithgow et al. | |
| 7,559,327 B2 * | 7/2009 | Hernandez | A61M 16/06 128/203.22 |
| 7,866,944 B2 | 1/2011 | Kenyon et al. | |
| 8,251,066 B1 * | 8/2012 | Ho | A61M 16/06 128/204.18 |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,138,553 B2 * | 9/2015 | Wood | A61M 16/0666 128/206.21 |
| 9,174,018 B2 * | 11/2015 | Ho | A61M 16/06 128/206.21 |
| 9,242,061 B2 * | 1/2016 | Lockhart | A61M 16/0816 128/200.24 |
| 9,295,805 B2 * | 3/2016 | Worboys | A61M 16/06 128/202.27 |
| 2003/0075180 A1 | 4/2003 | Raje et al. | |
| 2004/0255948 A1 * | 12/2004 | Smith | A61M 16/06 128/206.15 |
| 2008/0276937 A1 * | 11/2008 | Davidson | A61M 16/06 128/204.18 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0051034 A1 | 3/2010 | Howard et al. | |
| 2011/0023874 A1 | 2/2011 | Bath et al. | |
| 2012/0222680 A1 * | 9/2012 | Eves | A61M 16/0875 128/206.24 |
| 2013/0160769 A1 | 6/2013 | Ng et al. | |
| 2014/0347663 A1 * | 11/2014 | Rodes | G01N 1/2273 356/338 |

FOREIGN PATENT DOCUMENTS

| | | |
|---|---|---|
| WO | WO 98/004310 A1 | 2/1998 |
| WO | WO 98/034665 A1 | 8/1998 |
| WO | WO 2000/078381 A1 | 12/2000 |
| WO | WO 2002/051486 A1 | 7/2002 |
| WO | WO 2002/096342 A2 | 12/2002 |
| WO | WO 2004/073778 A1 | 9/2004 |
| WO | WO 2005/063328 A1 | 7/2005 |
| WO | WO 2006/074513 A1 | 7/2006 |
| WO | WO 2006/074516 A1 | 7/2006 |
| WO | WO 2006/130903 A1 | 12/2006 |
| WO | WO 2009/052560 A1 | 4/2009 |
| WO | WO 2009/108995 A1 | 9/2009 |
| WO | WO 2010/135785 A1 | 12/2010 |
| WO | WO 2012/109704 A1 | 8/2012 |
| WO | WO 2012/171072 A1 | 12/2012 |
| WO | WO 2013/020167 A1 | 2/2013 |
| WO | WO 2014/129913 A1 | 8/2014 |
| WO | WO 2014/138803 A1 | 9/2014 |

OTHER PUBLICATIONS

International Search Report issued in International PCT Application No. PCT/AU2014/050257 dated Nov. 26, 2014.
Written Opinion of the International Searching Authority issued in International PCT Application No. PCT/AU2014/050257 dated Nov. 26, 2014.
Written Opinion of the International Preliminary Examining Authority issued in International PCT Application No. PCT/AU2014/050257 dated Sep. 11, 2015.
Written Opinion of the International Preliminary Examination Authority issued in International PCT Application No. PCT/AU2014/050257 dated Nov. 30, 2015.
International Preliminary Report on Patentability issued in International PCT Application No. PCT/AU2014/050257 dated Jan. 20, 2016.
First Examination Report issued in corresponding New Zealand Application No. 616734 dated Oct. 23, 2013.
First Examination Report issued in corresponding New Zealand Application No. 631446 dated Sep. 25, 2014.
Further Examination Report issued in corresponding New Zealand Application No. 631446 dated Nov. 6, 2015.
Further Examination Report issued in corresponding New Zealand Application No. 631446 dated Feb. 23, 2016.
Further Examination Report dated Apr. 11, 2017 issued in New Zealand Application No. 718810 (2 pages).
First Examination Report issued in corresponding New Zealand Application No. 718810 dated May 2, 2016.
First Examination Report dated Sep. 25, 2017 issued in New Zealand Application No. 735482 (2 pages).
Office Action dated Sep. 14, 2018 issued in Taiwanese Application No. 103134489 with English translation (23 pages).

* cited by examiner

Nose - Anterolateral view

MASK VENT WITH SIDE WALL

1 CROSS-REFERENCE TO RELATED APPLICATIONS

This application is the U.S. national phase of International Application No. PCT/AU2014/050257 filed 30 Sep. 2014, which designated the U.S. and claims priority to AU Patent Application No. 2013903819 filed 3 Oct. 2013, the entire contents of each of which are hereby incorporated by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE INVENTION 5.1 Field of the Invention

The present technology relates to one or more of the diagnosis, treatment, prevention, and amelioration of respiratory disorders. In particular, the present technology relates to medical devices, and their use for treating respiratory disorders and for preventing respiratory disorders.

5.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the Essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation during sleep, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

5.2.1 Systems

One known product used for treating sleep disordered breathing is the S9 Sleep Therapy System, manufactured by ResMed.

5.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

5.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use, and uncomfortable especially when worn for long periods of time or when a patient is unfamiliar with a system. Masks designed solely for aviators as part of personal protection equipment or for the administration of anaesthetics may be tolerable for their original application, but nevertheless be undesirably uncomfortable to be worn for extended periods, for example, while sleeping.

5.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

5.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

5.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078.381; U.S. Pat. No. 6,581,594; US Patent Application; US 2009/0050156; US Patent Application 2009/0044808.

Table of noise of prior masks (ISO 17510-2:2007, 10 cmH$_2$O pressure at 1 metre):

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(*) one specimen only, measured using test method specified in ISO3744 in CPAP mode at 10 cmH$_2$O)

Sound pressure values of a variety of objects are listed below:

| Object | A-weighted sound pressure dbA (uncertainty) | Notes |
|---|---|---|
| Vacuum cleaner: Nilfisk Walter Broadly Litter Hog; B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

5.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130.903 (describing amongst other things aspects of ResMed LIBERTY full-face mask); International Patent Application WO 2009/052,560 (describing amongst other things aspects of ResMed SWIFT FX nasal pillows).

5.2.4 PAP Device

The air at positive pressure is typically supplied to the airway of a patient by a PAP device such as a motor-driven blower. The outlet of the blower is connected via a flexible delivery conduit to a patient interface as described above.

5.2.5 Mandibular Repositioning

A mandibular repositioning device (MRD) is one of the treatment options for sleep apnea. It is a custom made, adjustable oral appliance available from a dentist that holds the lower jaw in a forward position during sleep. This mechanical protrusion expands the space behind the tongue, puts tension on the pharyngeal walls to reduce collapse of the airway and diminishes palate vibration.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Another aspect of the present technology relates to a gas washout vent for a mask system structured to disperse or diffuse the exhaust vent flow, e.g., to reduce air jetting and noise.

Another aspect of the present technology relates to a gas washout vent including a side wall or hood at least partly surrounding one or more vent holes to disperse or diffuse the exhaust vent flow.

Another aspect of the present technology relates to a vent arrangement for a mask system including a mask component and a mask vent provided to the mask component. The mask vent includes a plurality of vent holes each extending through a thickness of the mask component and each including a vent exit, and a continuous side wall structured to surround the plurality of vent exits of the vent holes.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

7.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

7.2 Therapy

7.2.1 Respiratory System

Figure 1A:
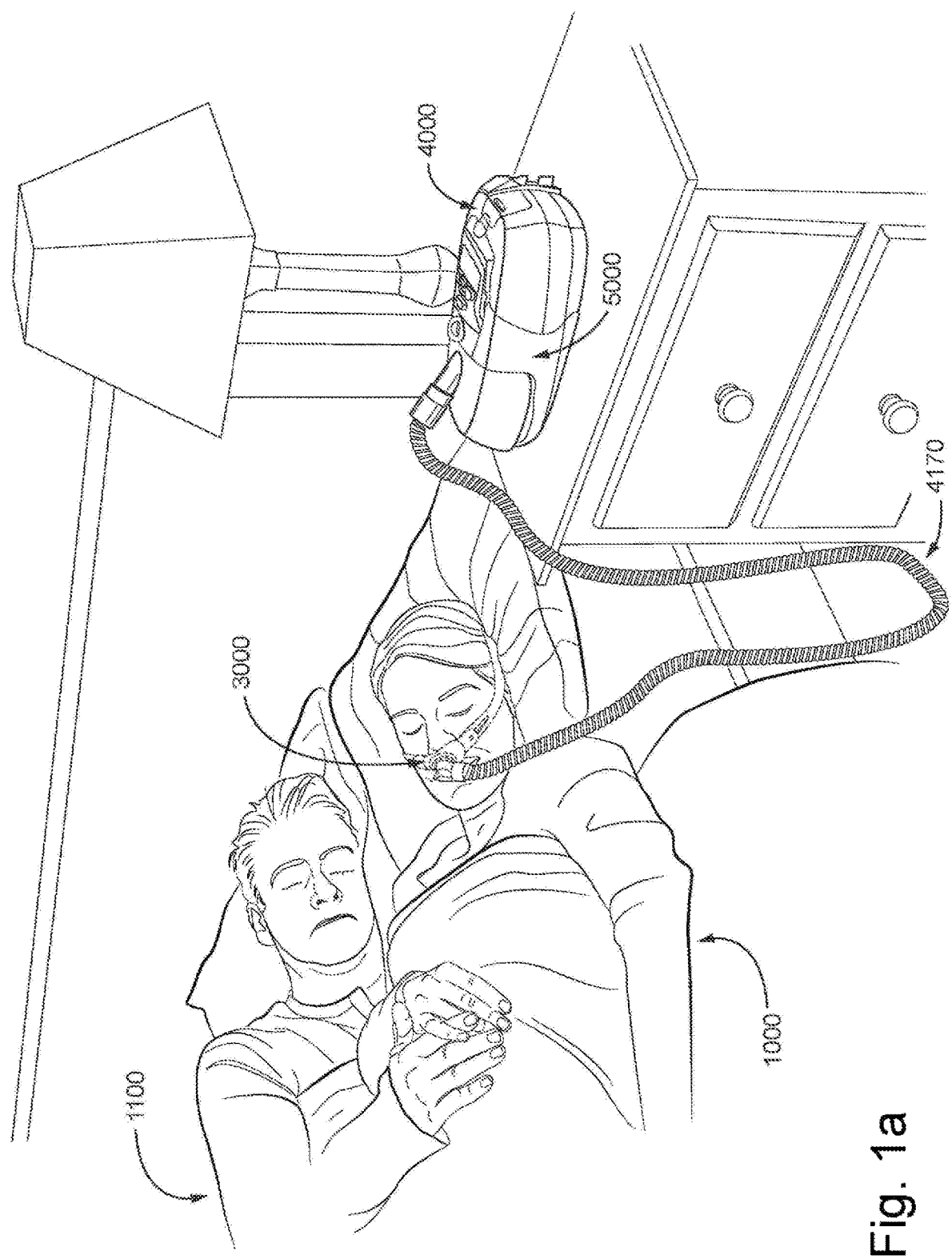
FIG. 1b shows a PAP device 4000 in use on a patient 1000 with a nasal mask 3000.
FIG. 1c shows a PAP device 4000 in use on a patient 1000 with a full-face mask 3000.
Figure 1B:
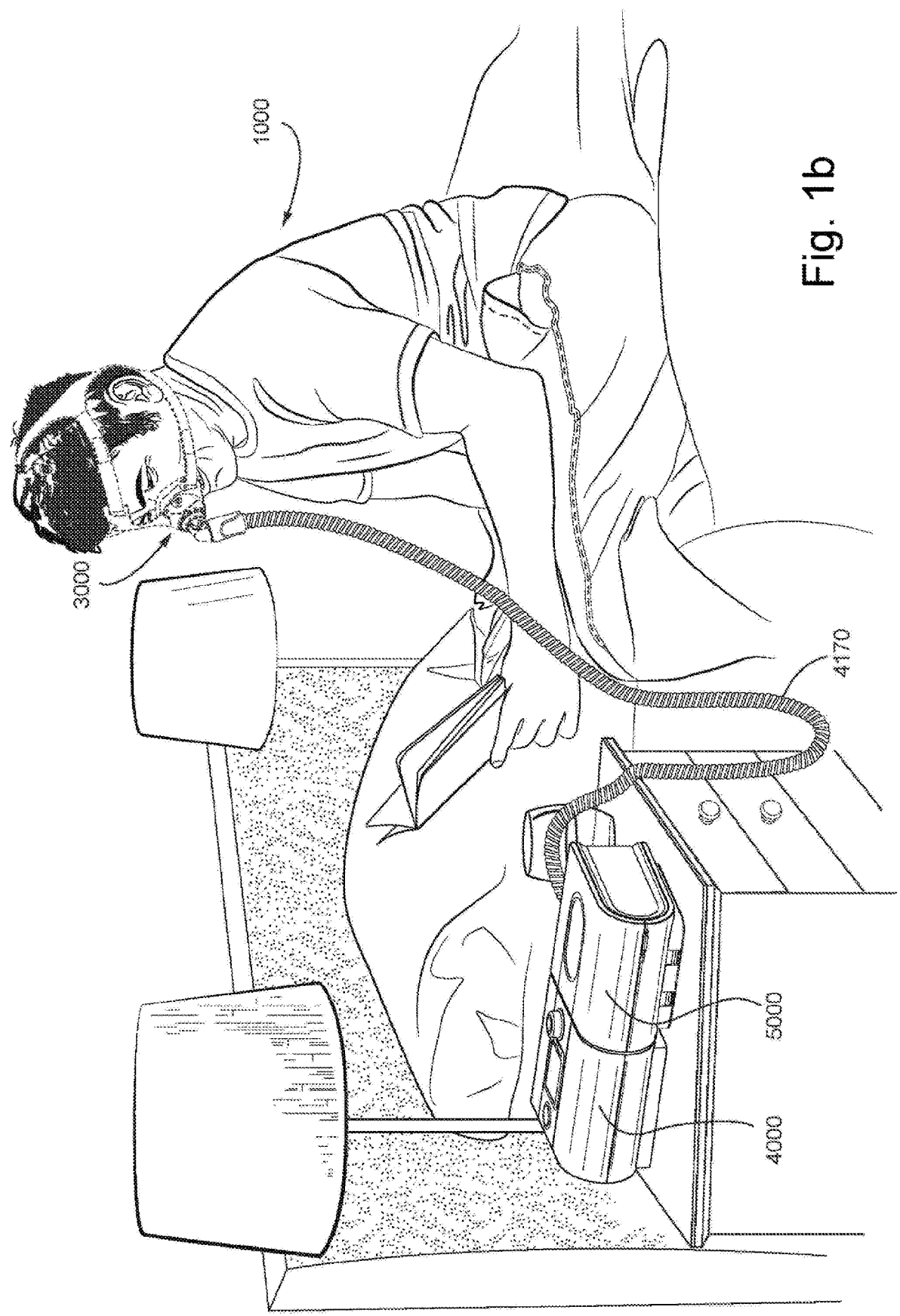
Figure 1C:
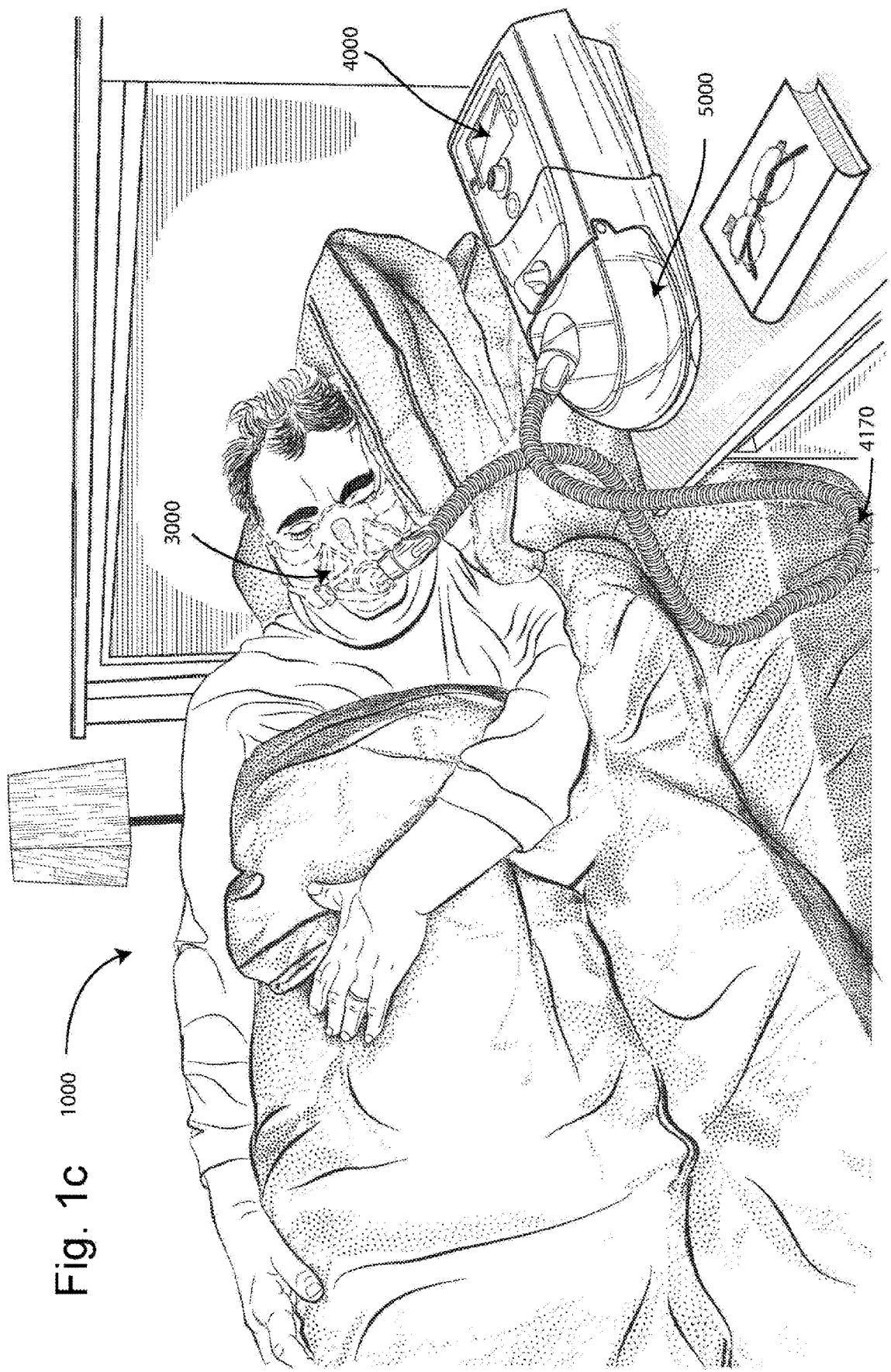
Figure 2A:
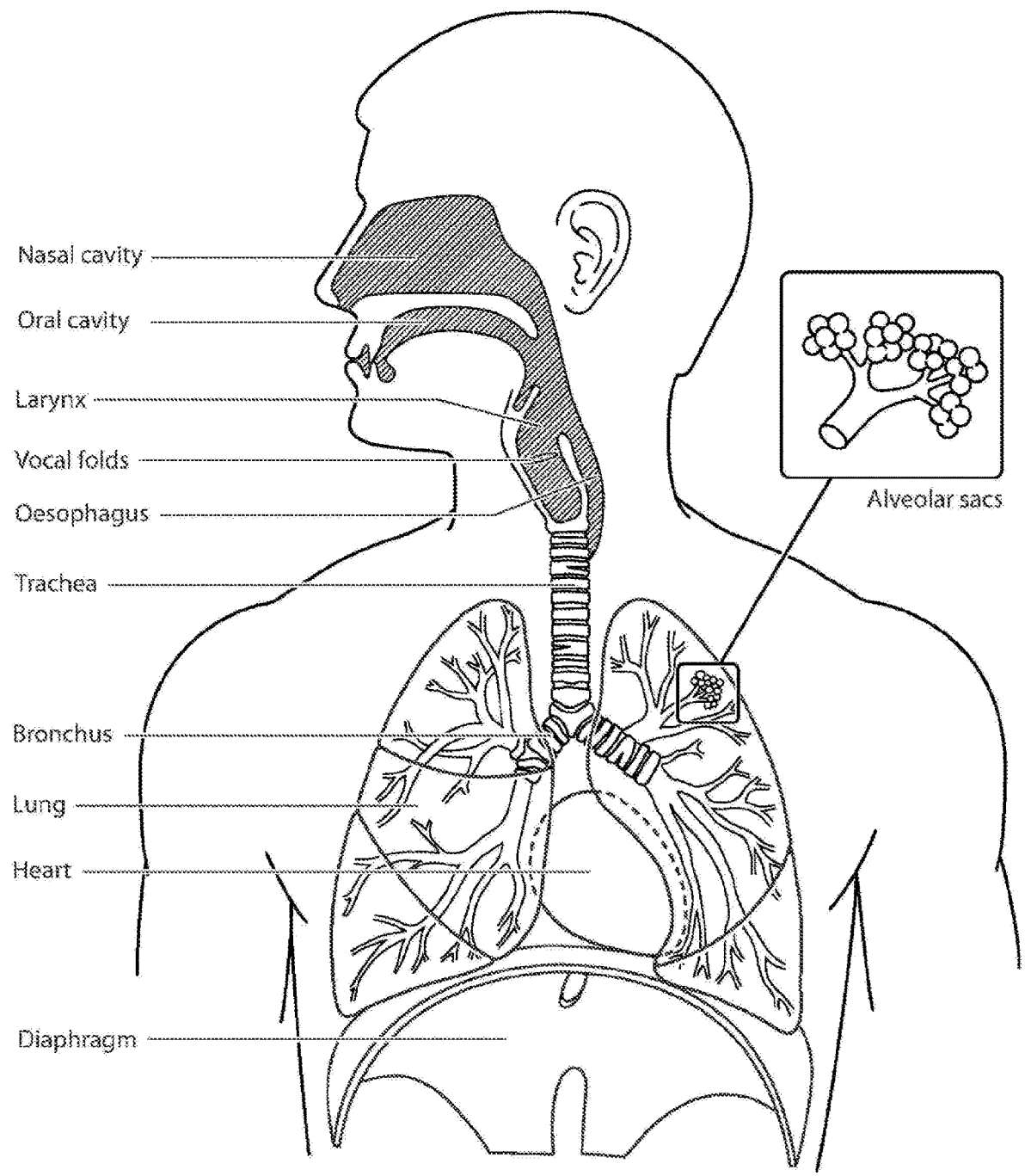

FIG. 2a shows an overview of a human respiratory system including the nasal and oral cavities, the larynx, vocal folds, oesophagus, trachea, bronchus, lung, alveolar sacs, heart and diaphragm.

Figure 2B:
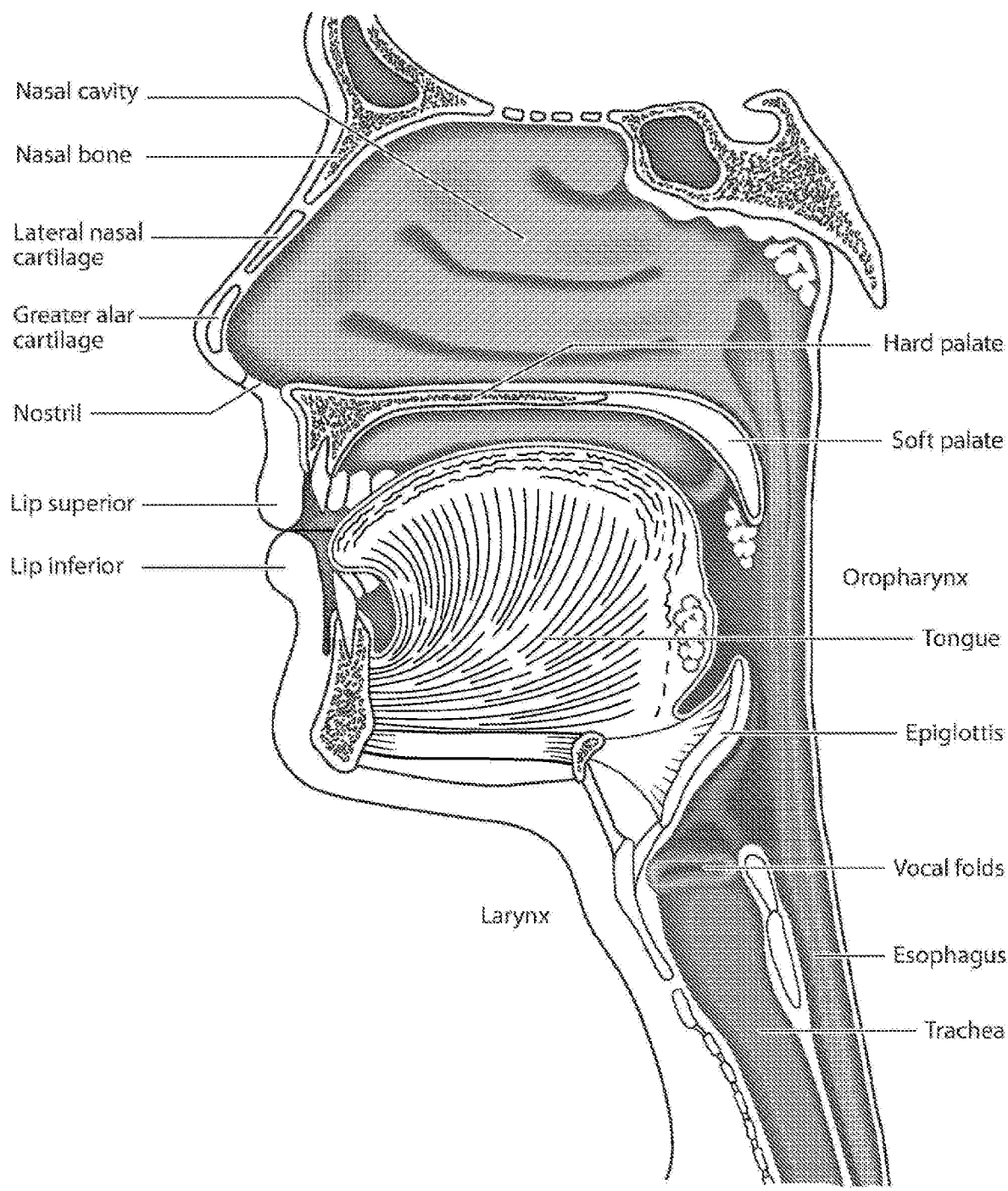

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

7.2.2 Facial Anatomy

Figure 2C:
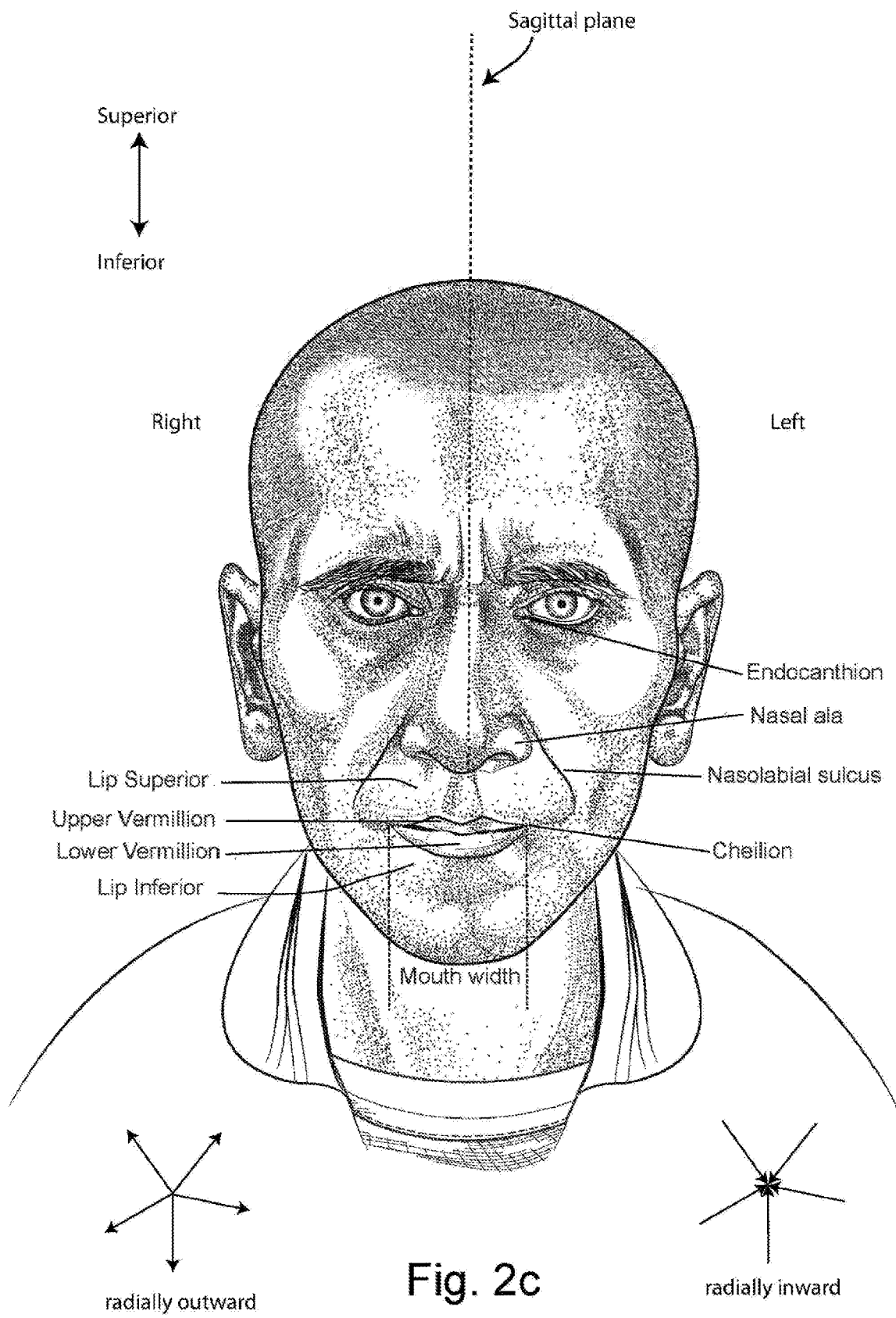

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
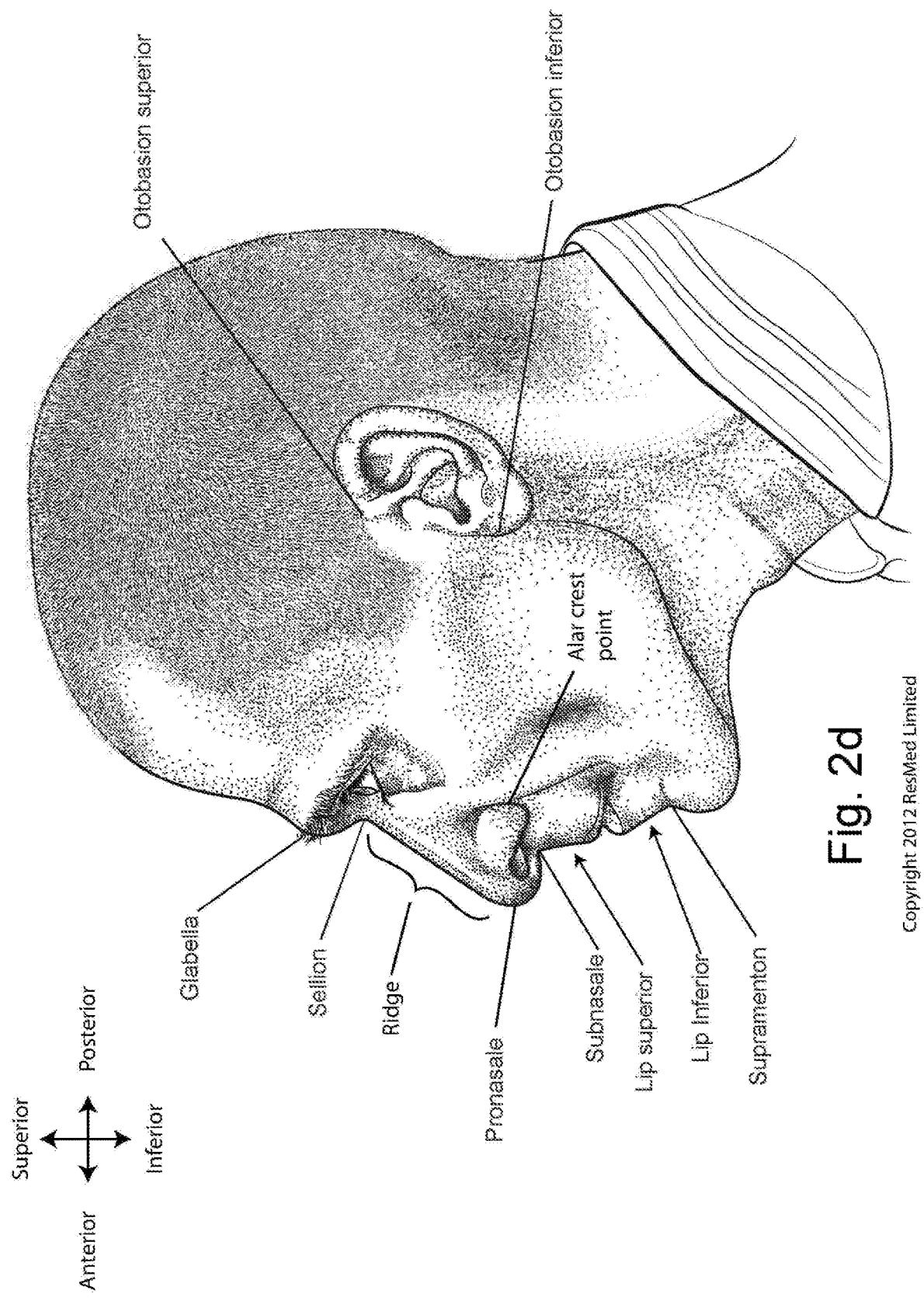

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
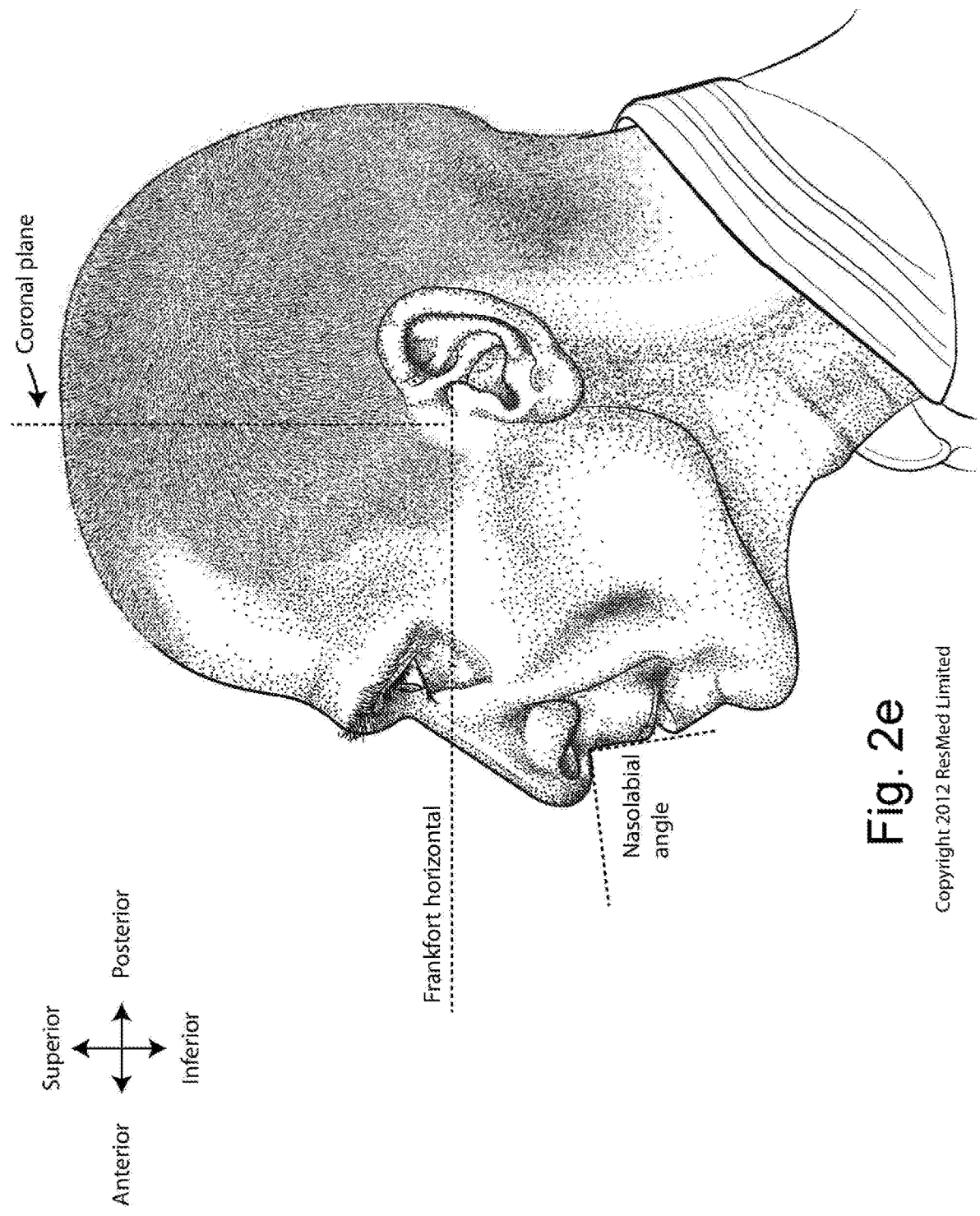

FIG. 2e is a further side view of a head. The approximate locations of the Frankfort horizontal and nasolabial angle are indicated.

Figure 2F:
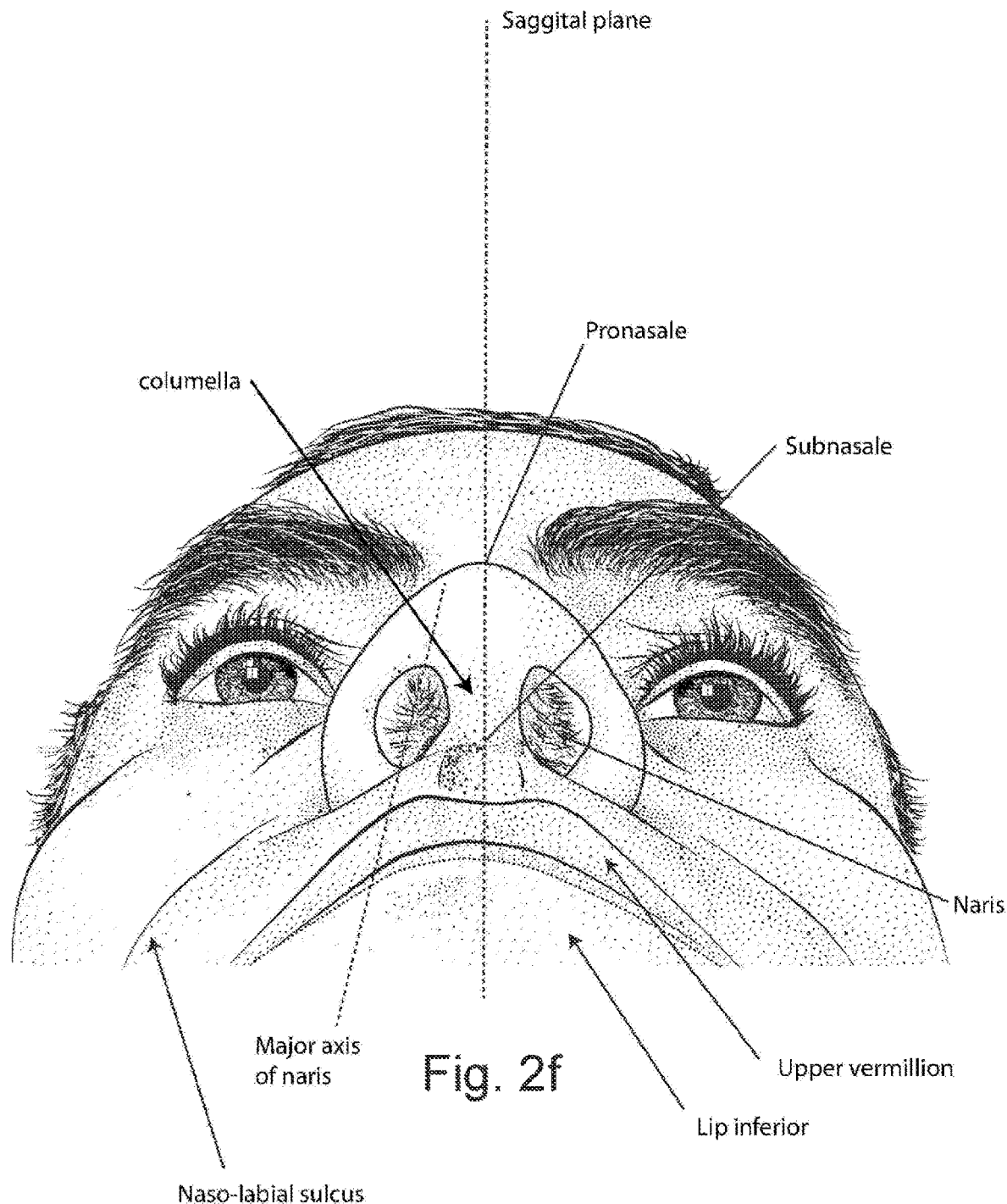

FIG. 2f shows a base view of a nose.

Figure 2I:
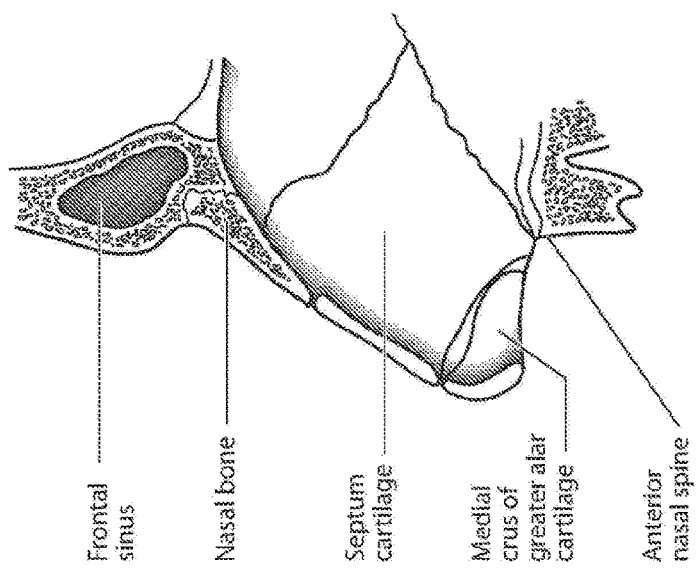
Figure 2H:
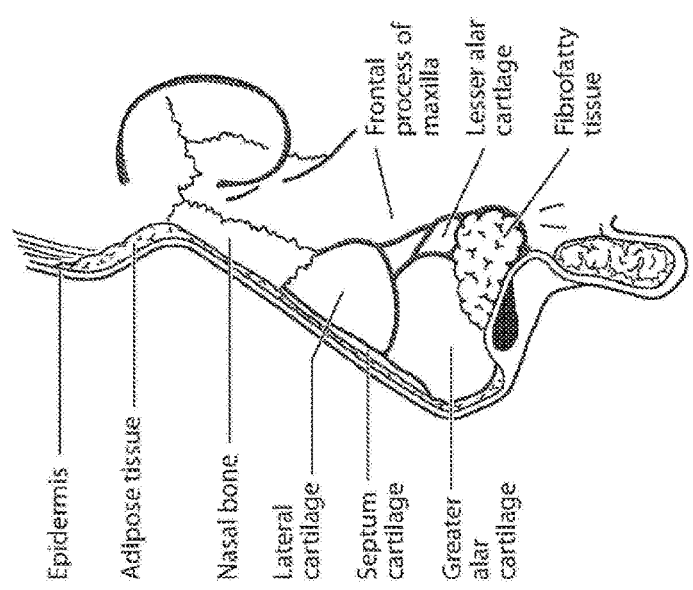
Figure 2G:
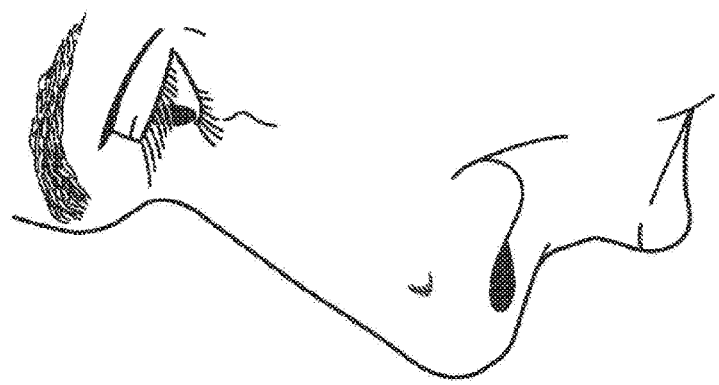

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figures 2J, 2K:
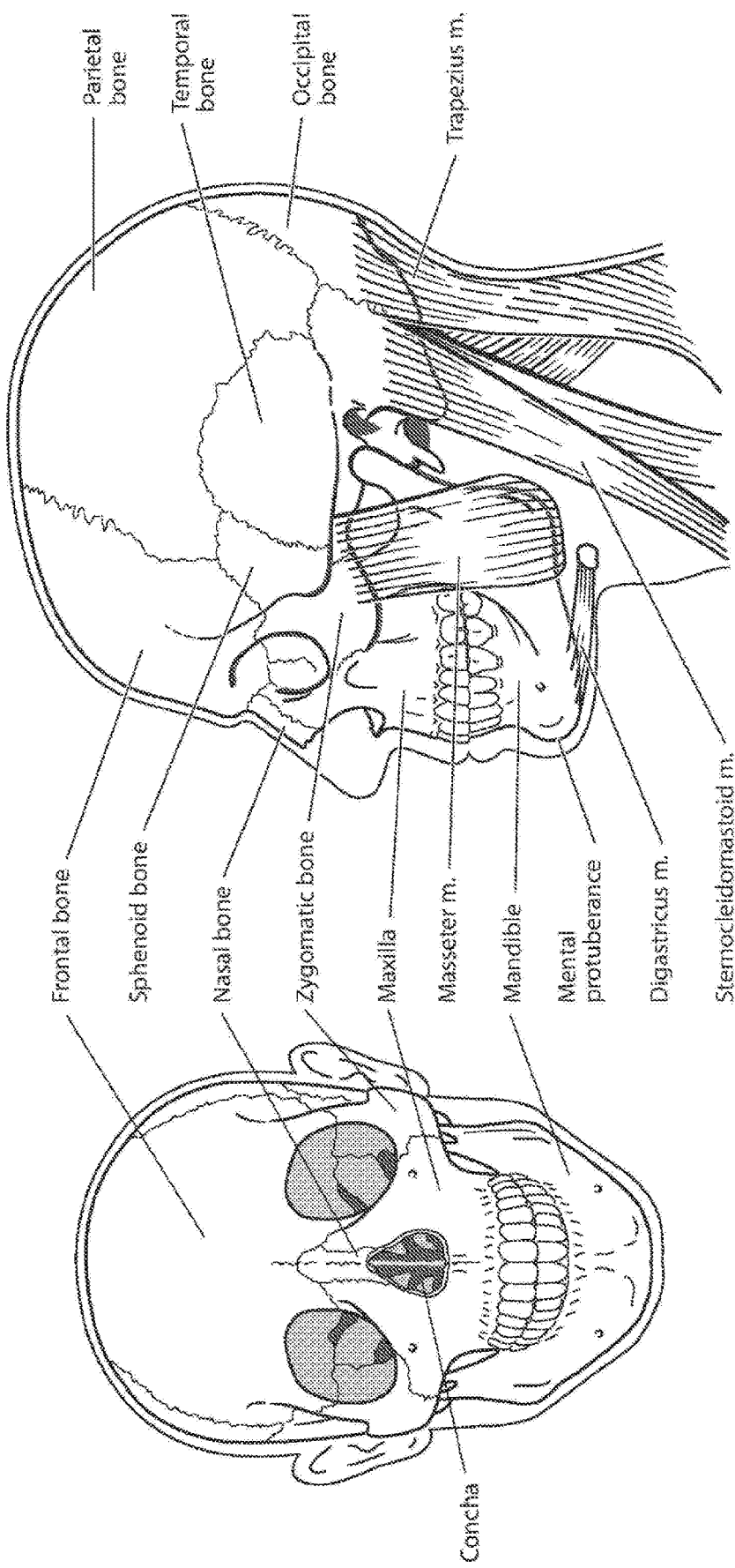
Figure 2I:
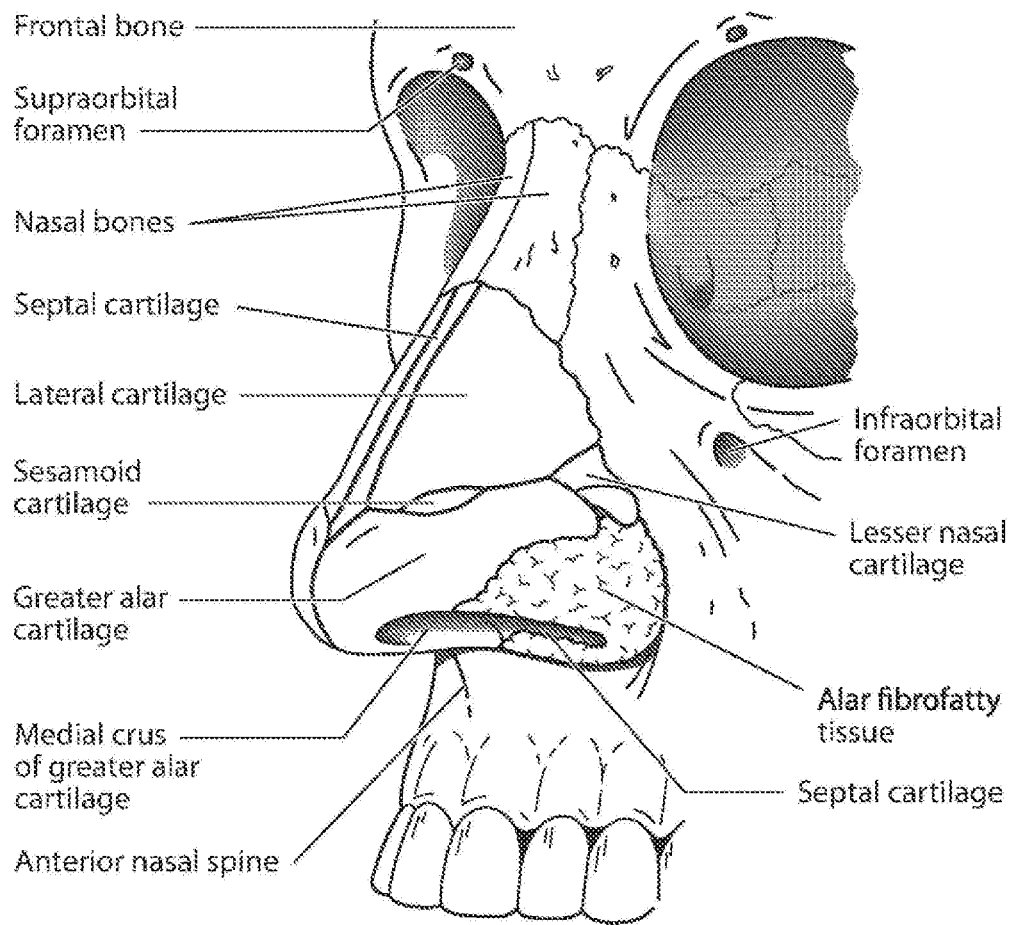

FIG. 2j shows a front view of the bones of a skull including the frontal, temporal, nasal and zygomatic bones. Nasal concha are indicated, as are the maxilla, mandible and mental protuberance.

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows an anterolateral view of a nose.

7.3 Patient Interface

Figures 1, 3:
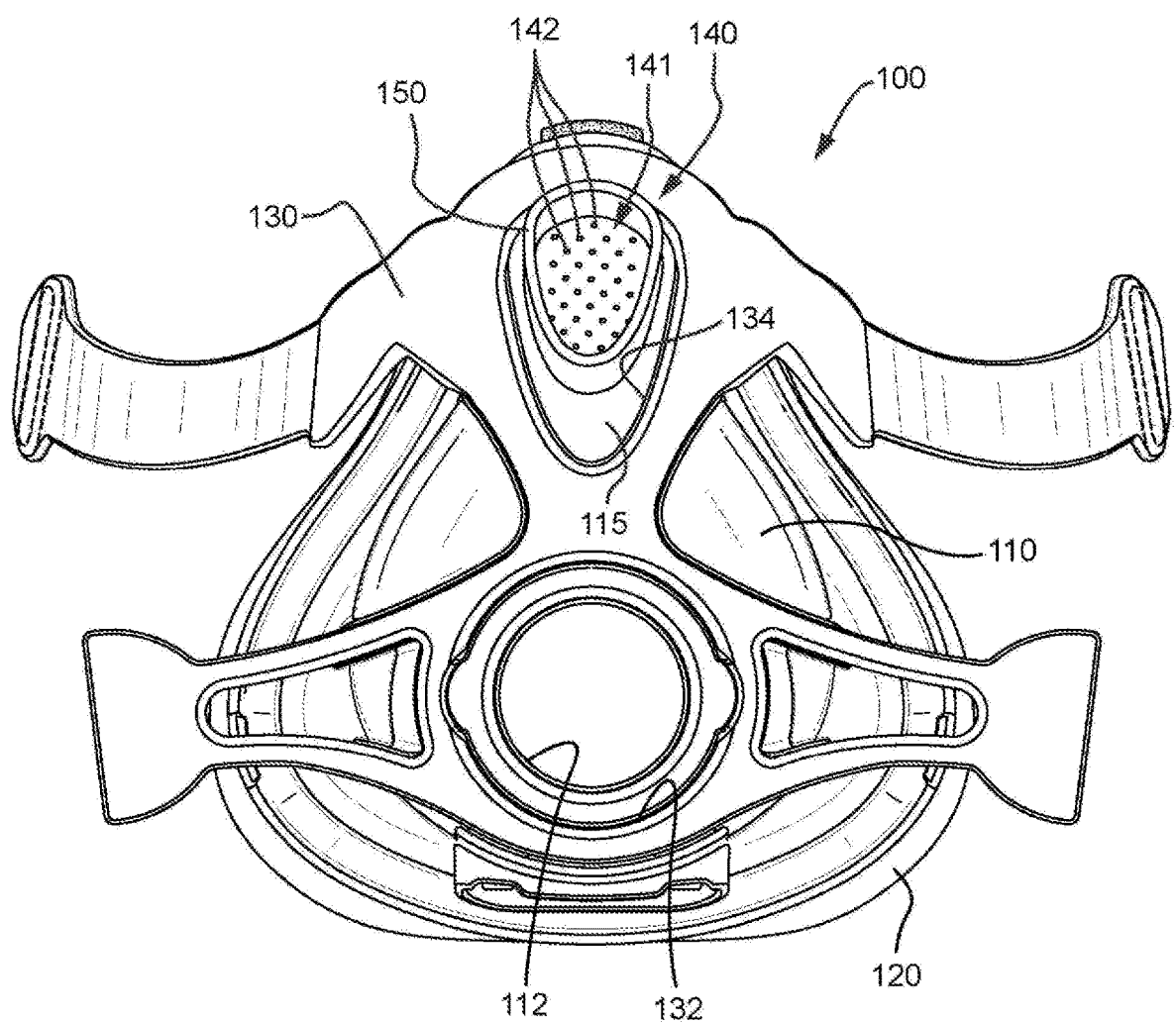

FIG. 3-1 shows mask system including a mask vent according to an example of the present technology.

Figures 2, 3:
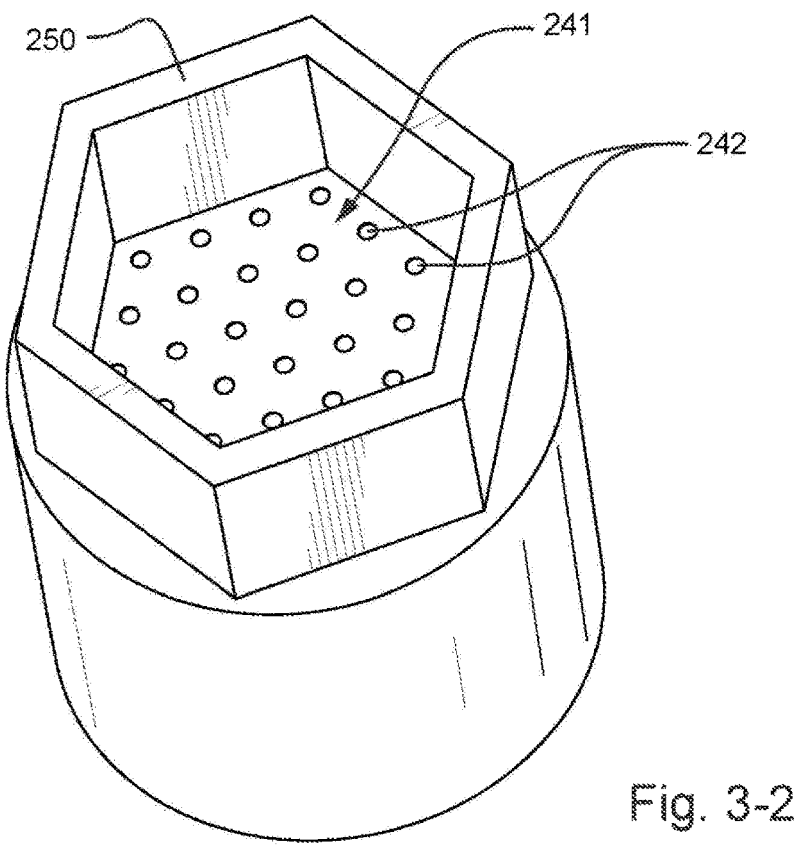
Figure 3:
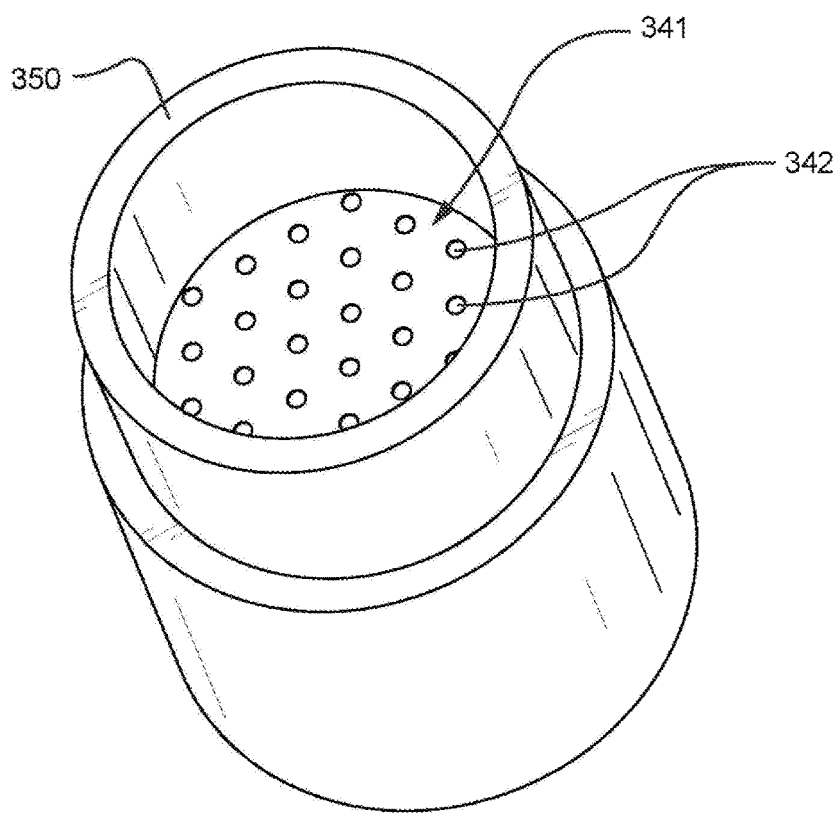

FIG. 3-2 shows a mask vent according to an example of the present technology.

FIG. 3-3 shows a mask vent according to an example of the present technology.

Figures 3, 4:
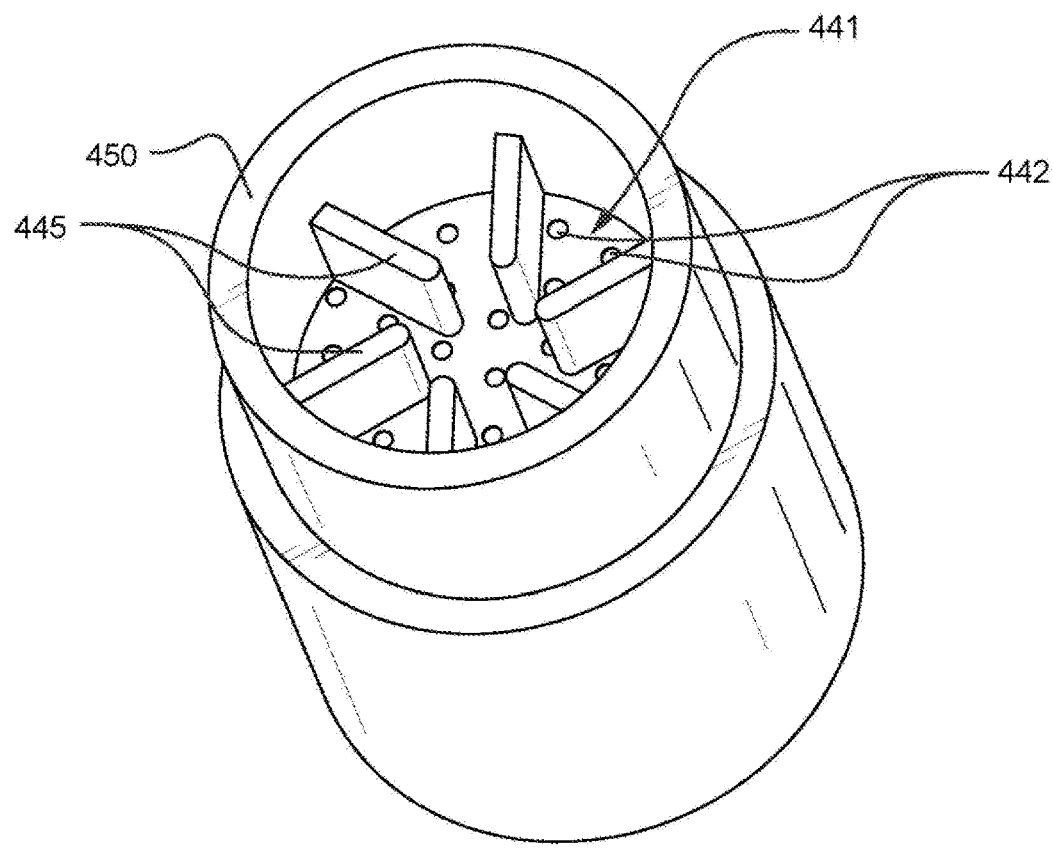
Figures 1, 3, 4, 5:
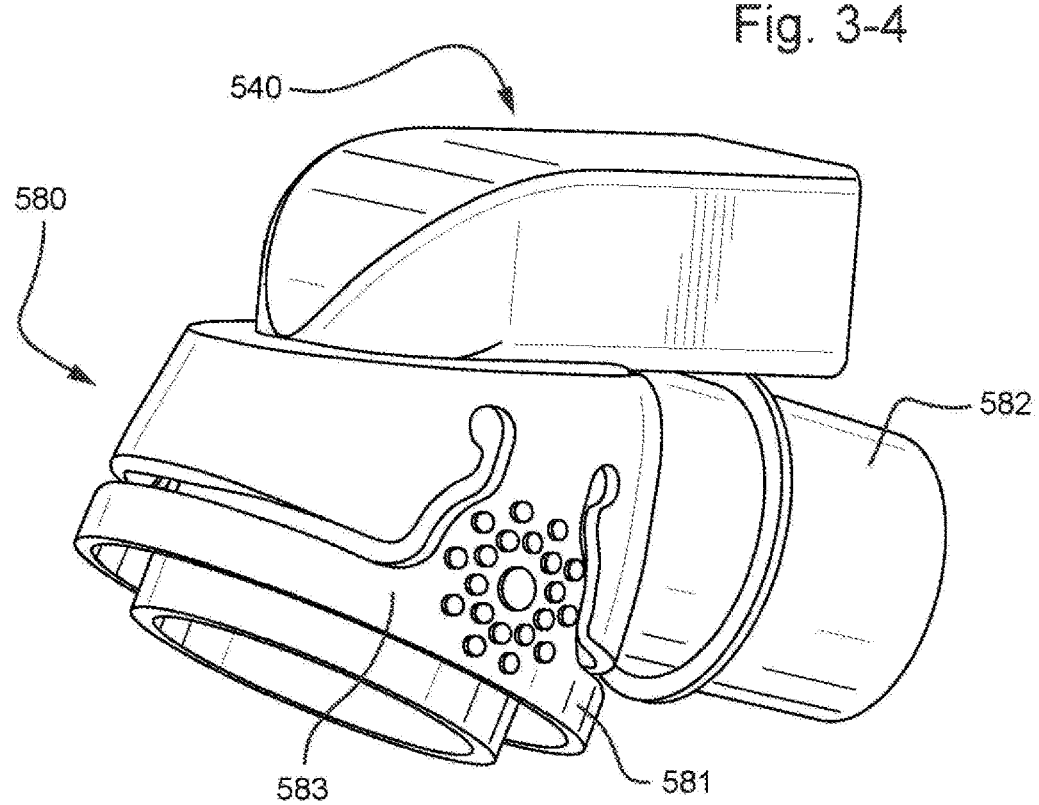
Figures 2, 3, 4, 5:
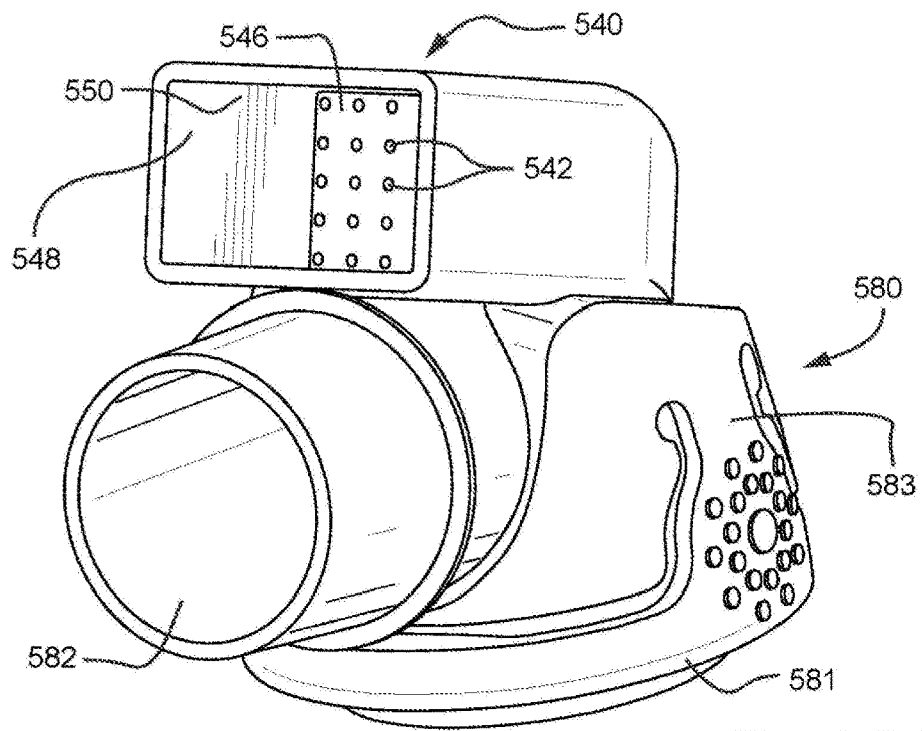
Figures 3, 4, 5:
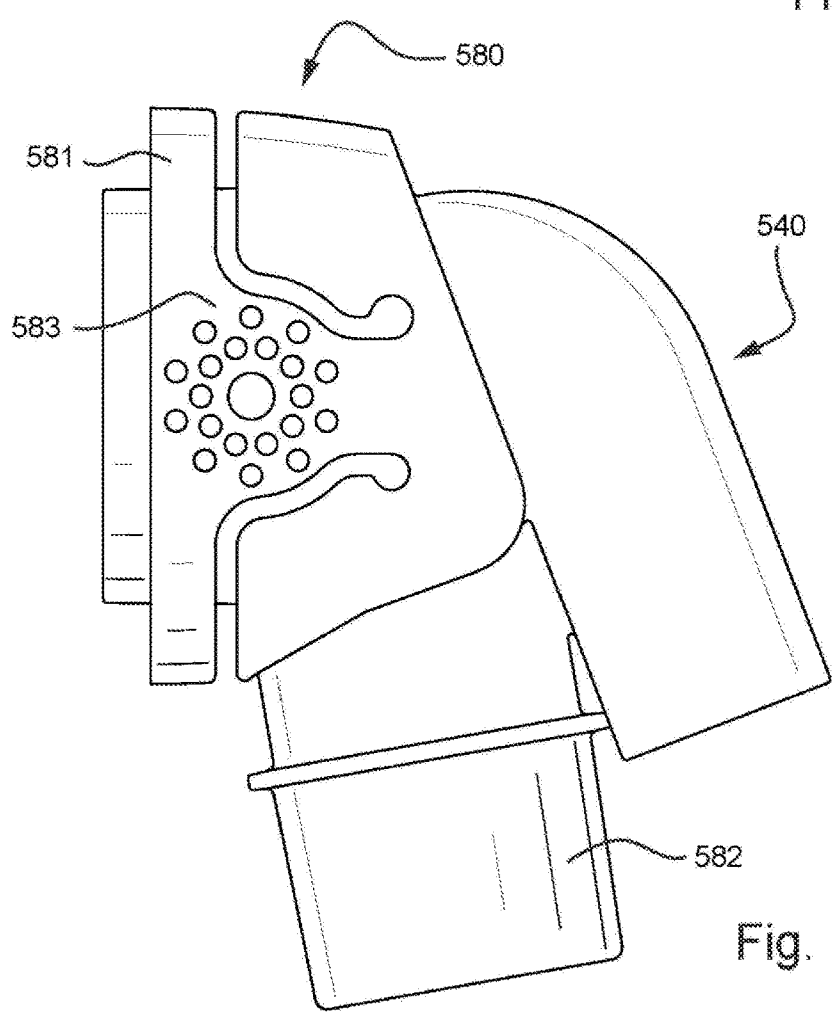
Figures 3, 4, 5:
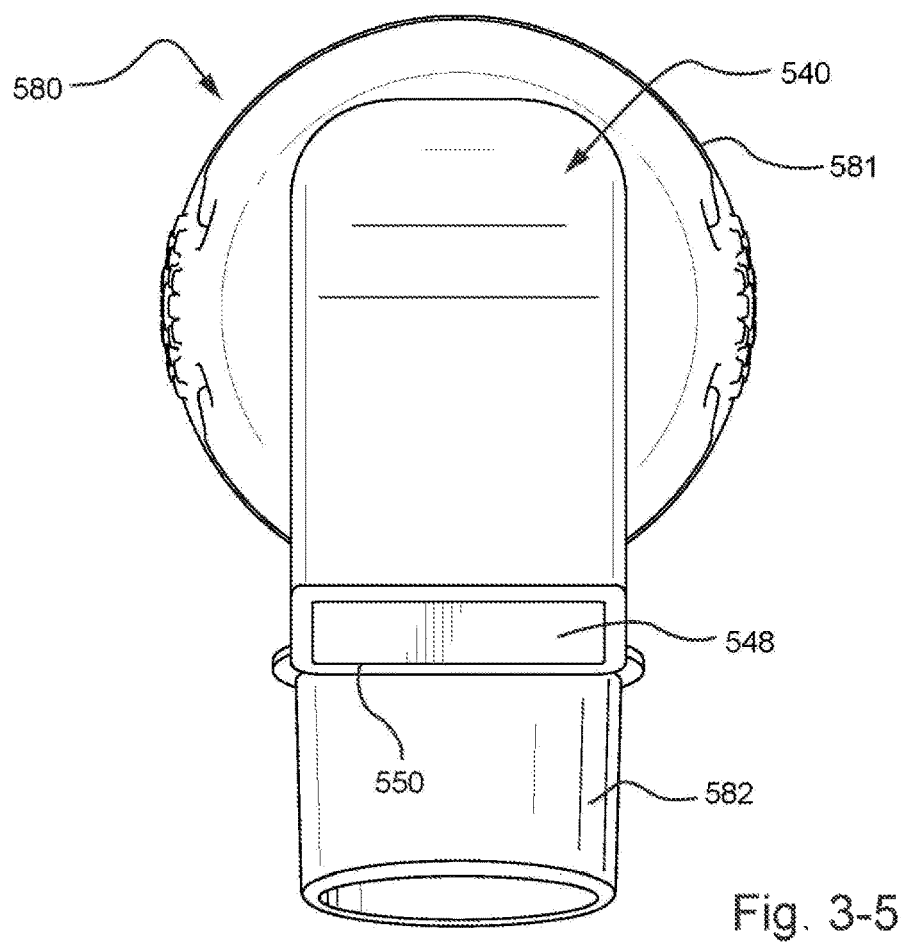
Figures 3, 4, 5:
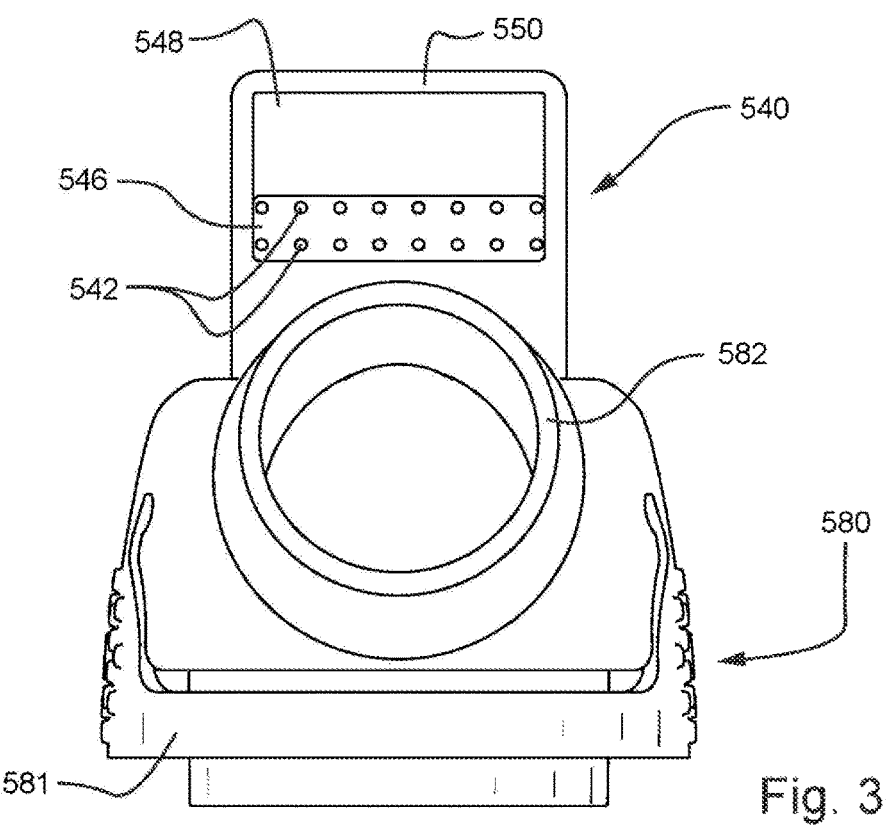
Figures 3, 4, 5, 6:
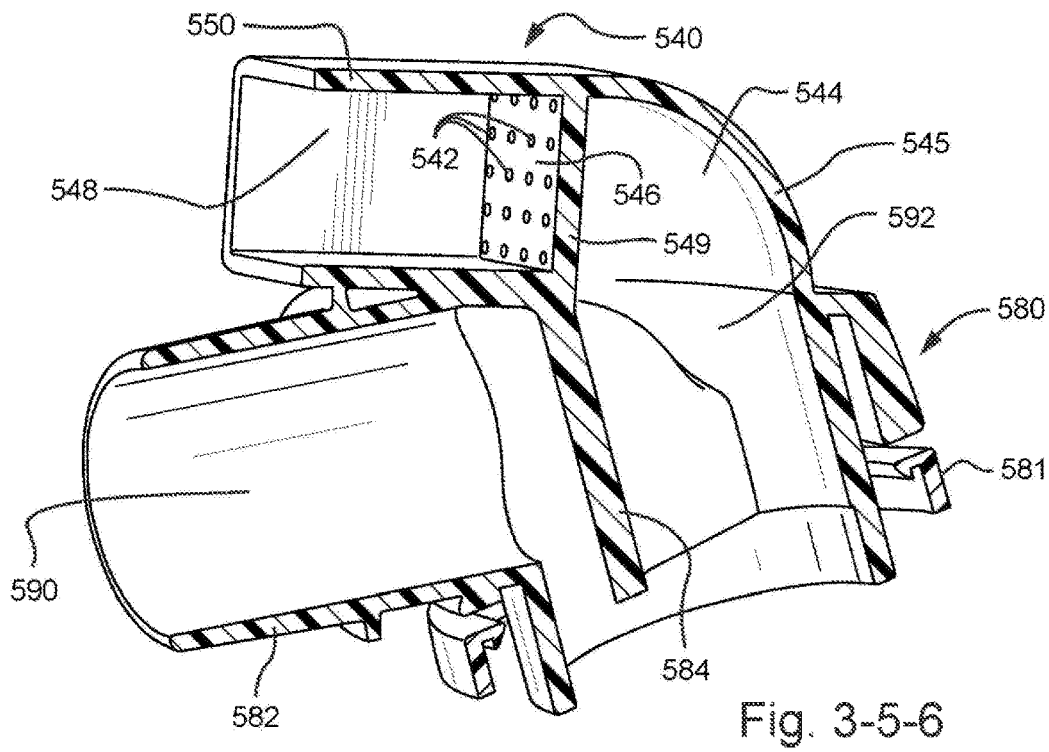
Figures 3, 4, 5, 7:
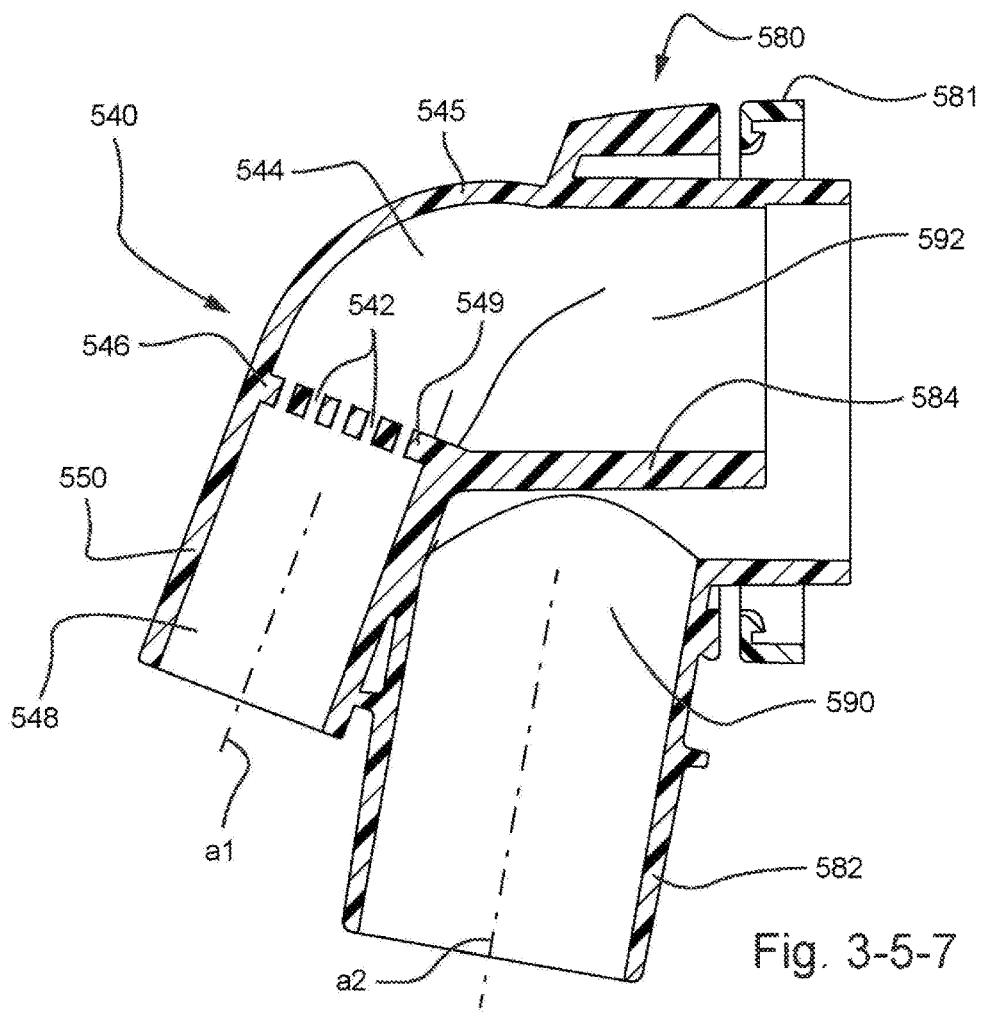
Figures 1, 3, 4, 5, 6:
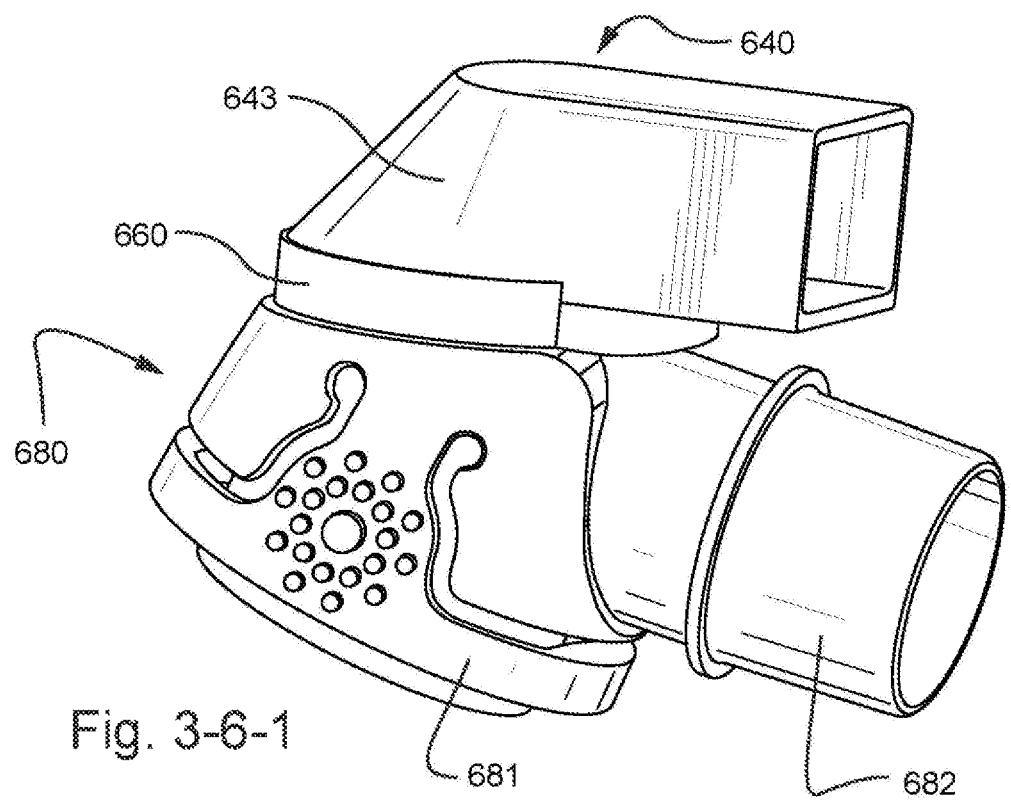
Figures 2, 3, 4, 5, 6:
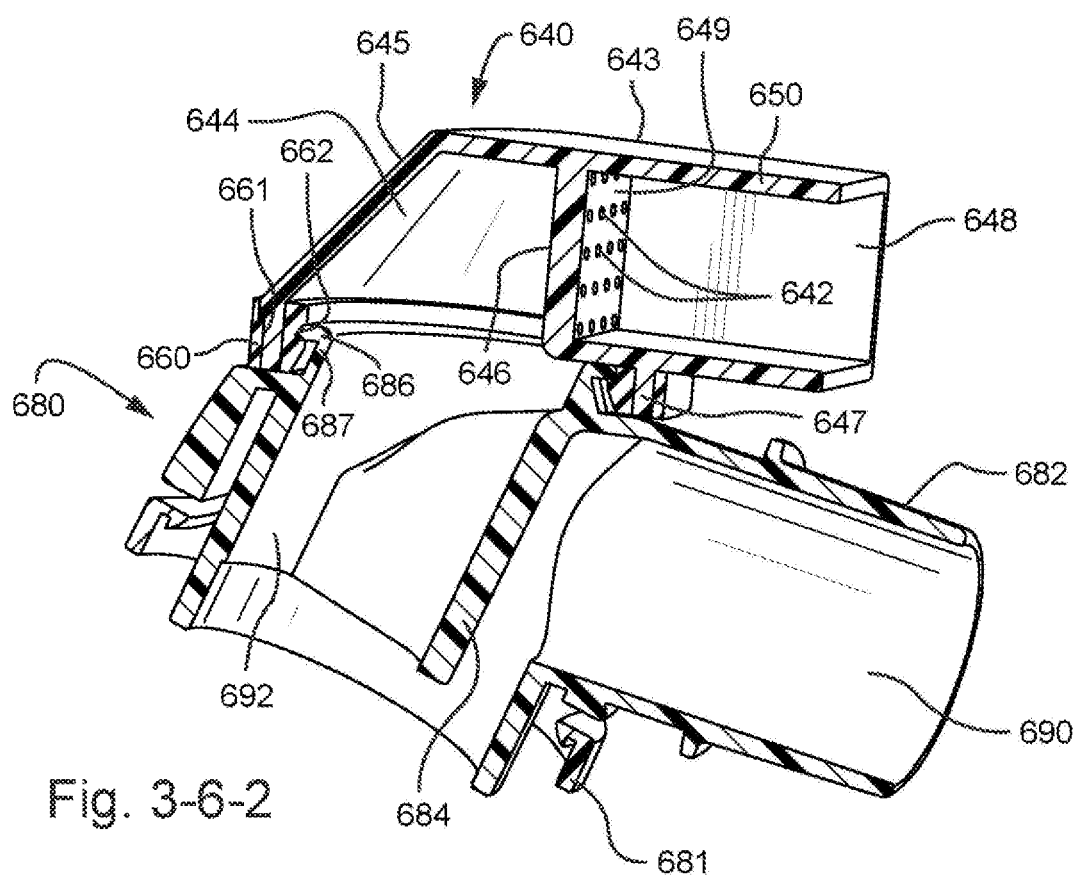
Figures 3, 4, 5, 6:
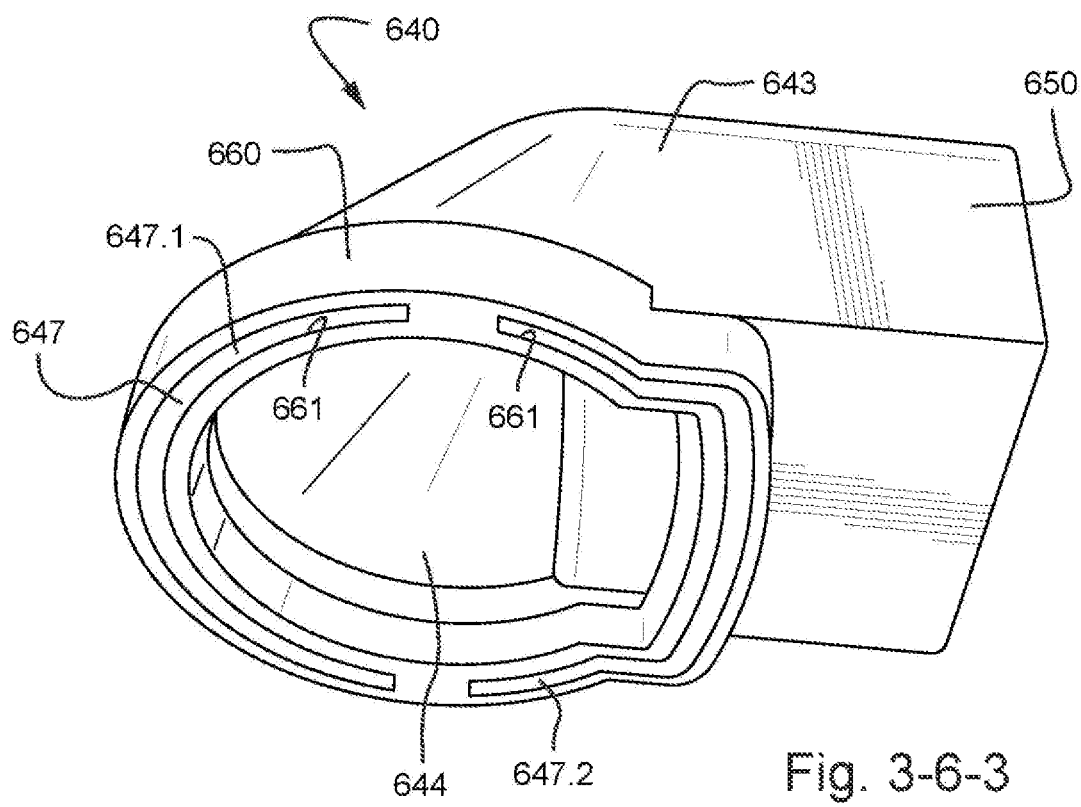
Figures 3, 4, 5, 6:
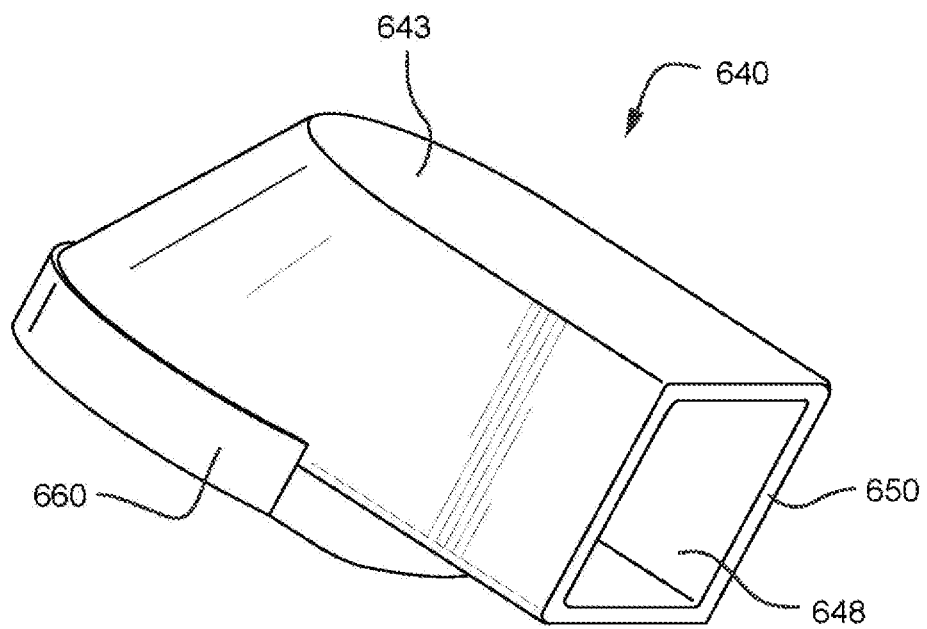
Figures 3, 4, 5, 6:
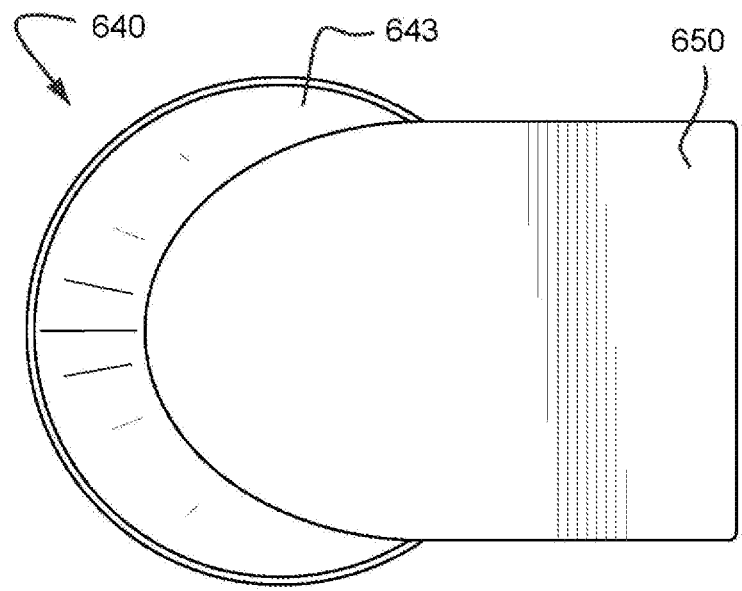
Figures 3, 4, 5, 6:
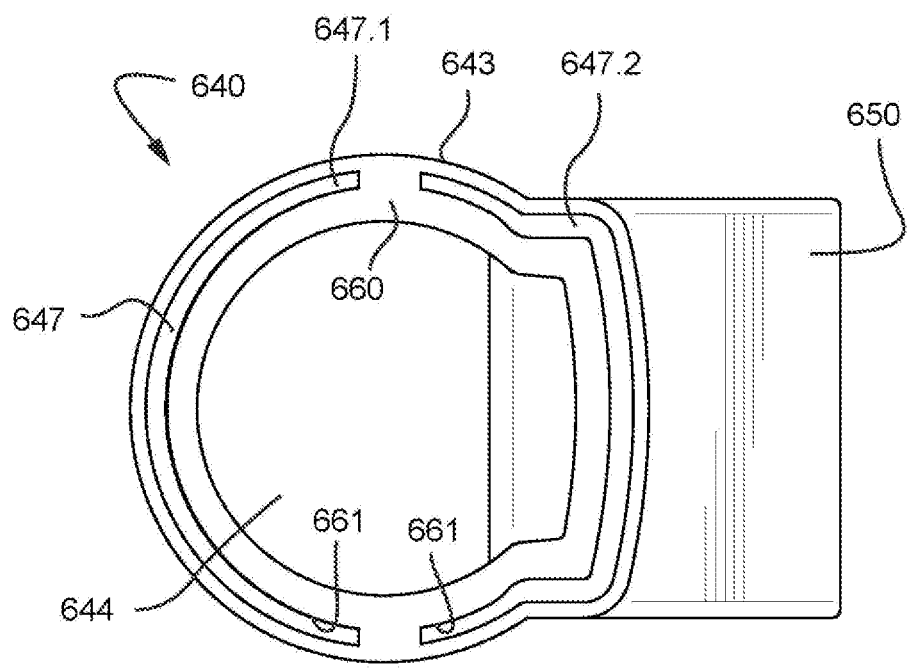
Figures 3, 4, 5, 6, 7:
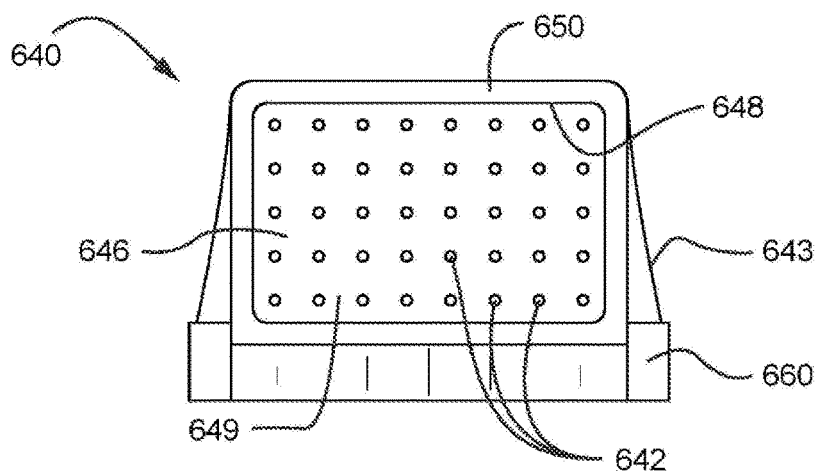
Figures 3, 4, 5, 6, 8:
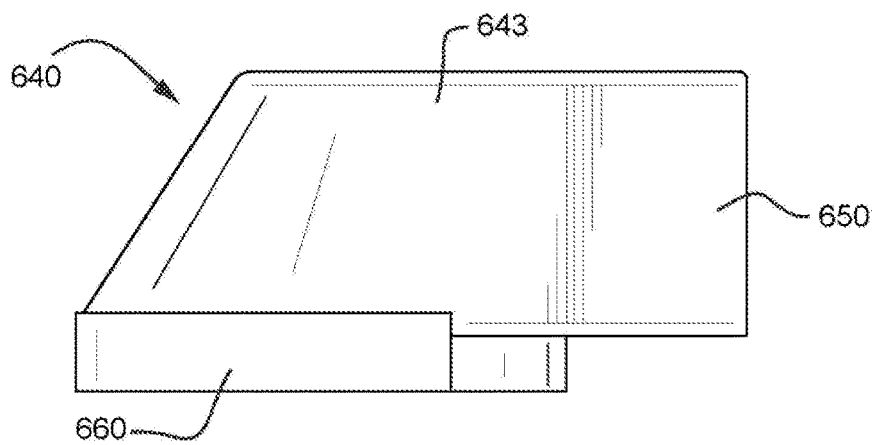
Figures 3, 4, 5, 6, 9:
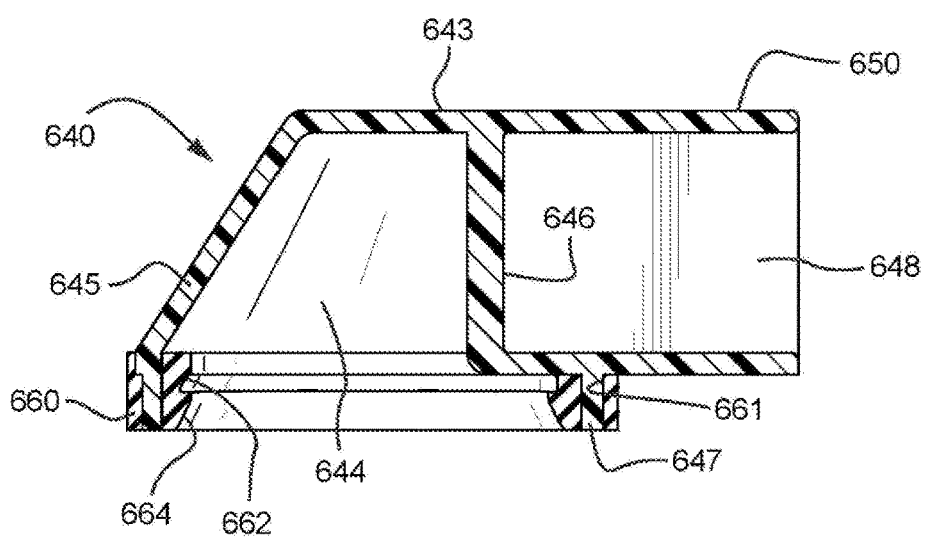
Figures 1, 3, 4, 5, 6, 7:
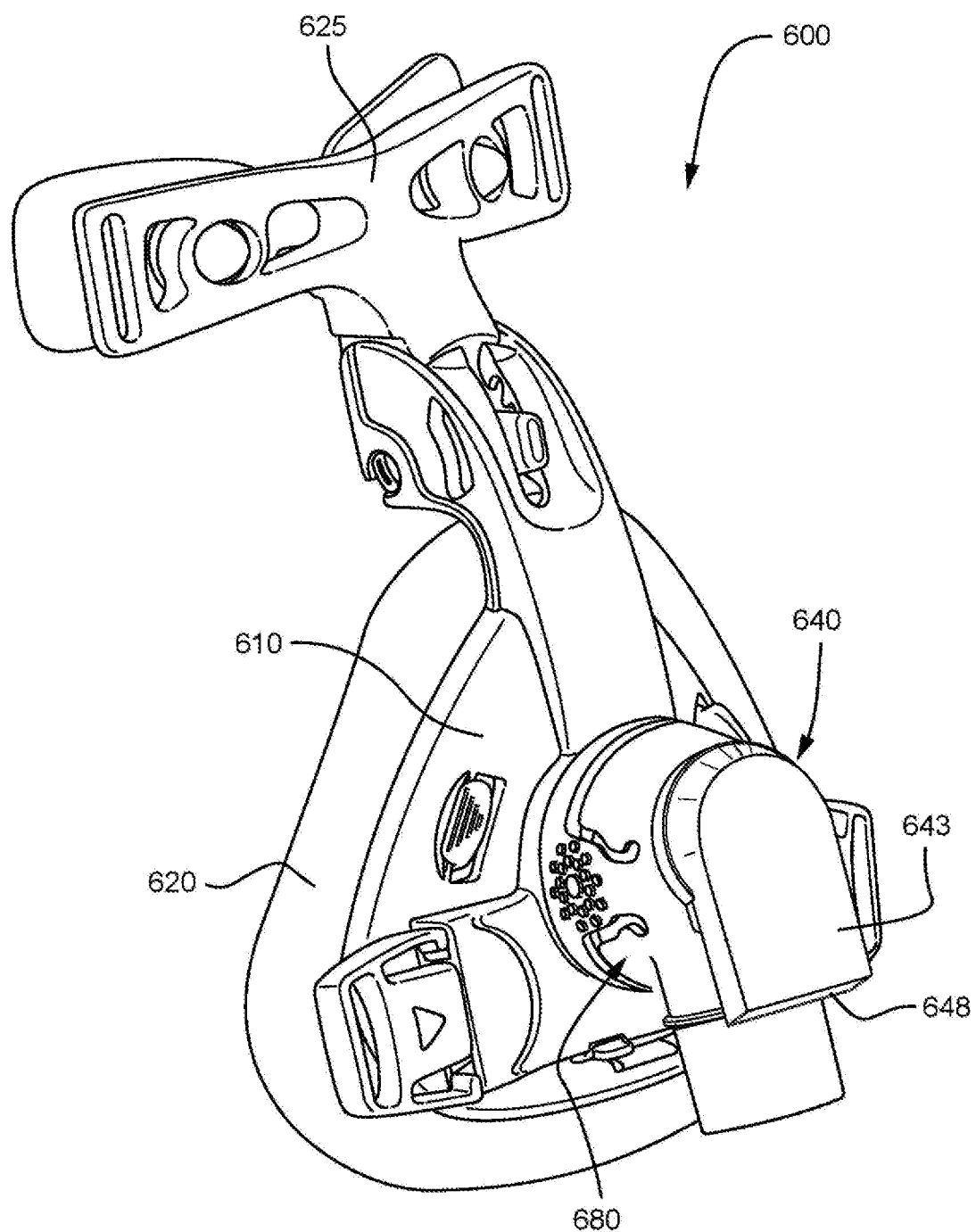
Figures 2, 3, 4, 5, 6, 7:
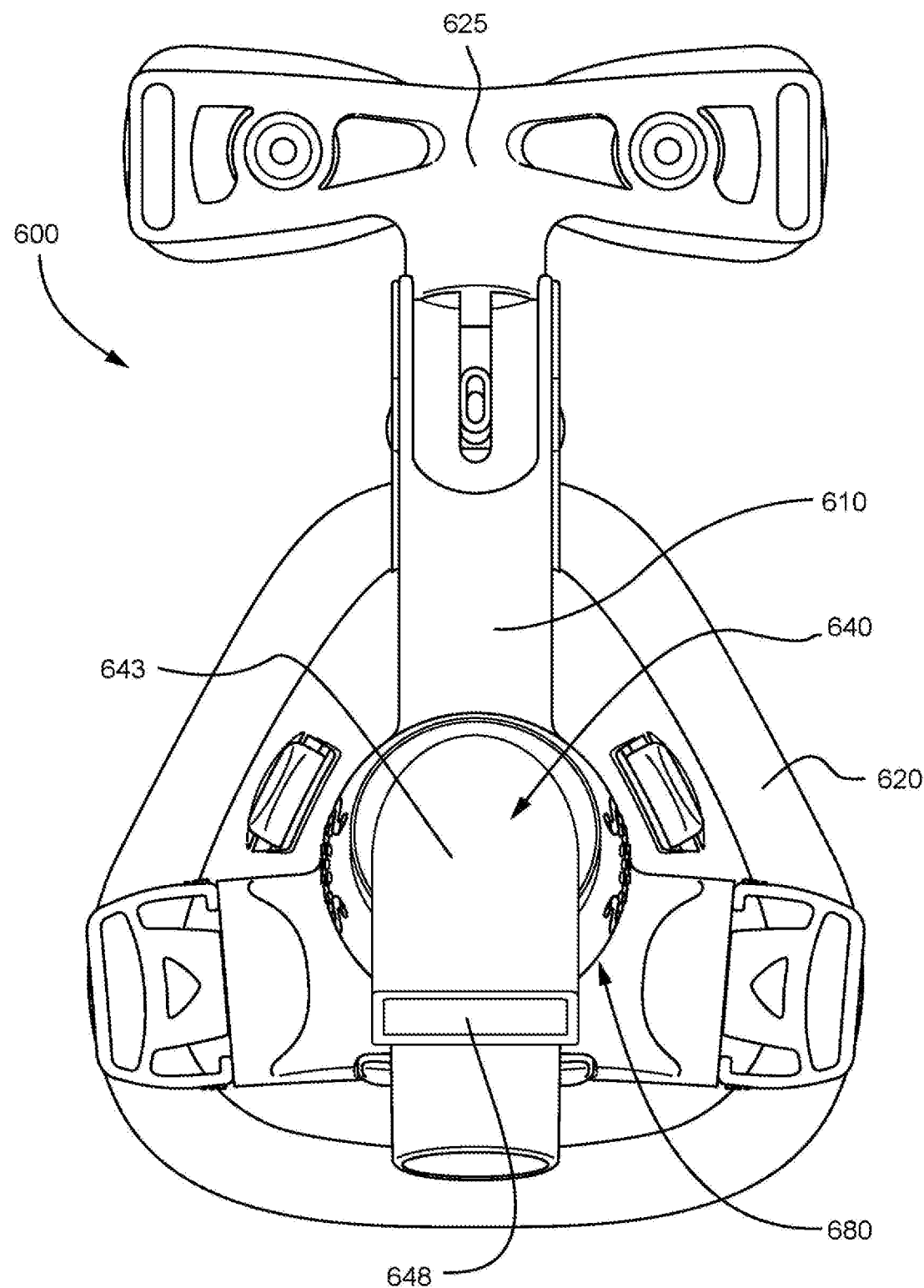
Figures 3, 4, 5, 6, 7:
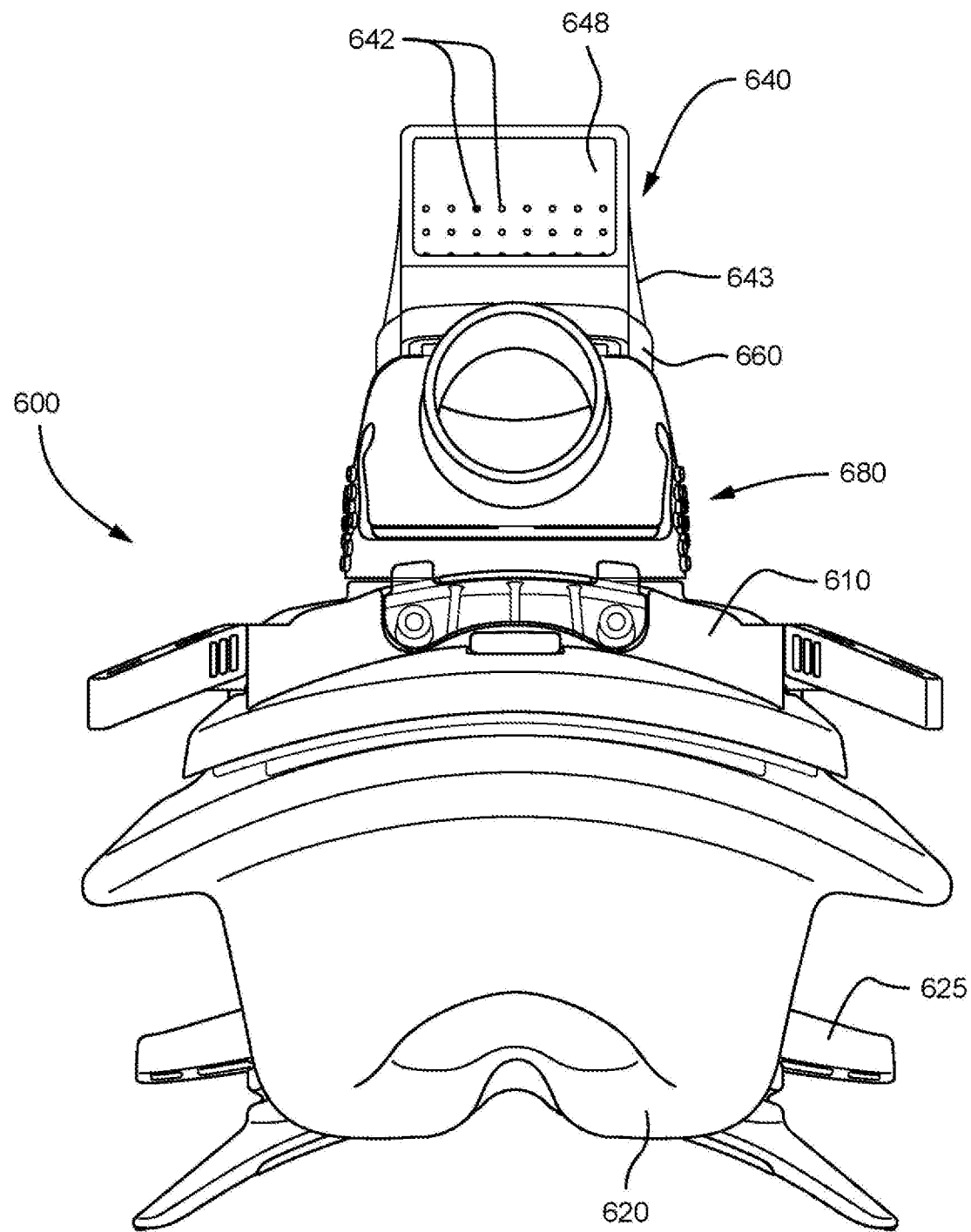
Figures 3, 4, 5, 6, 7:
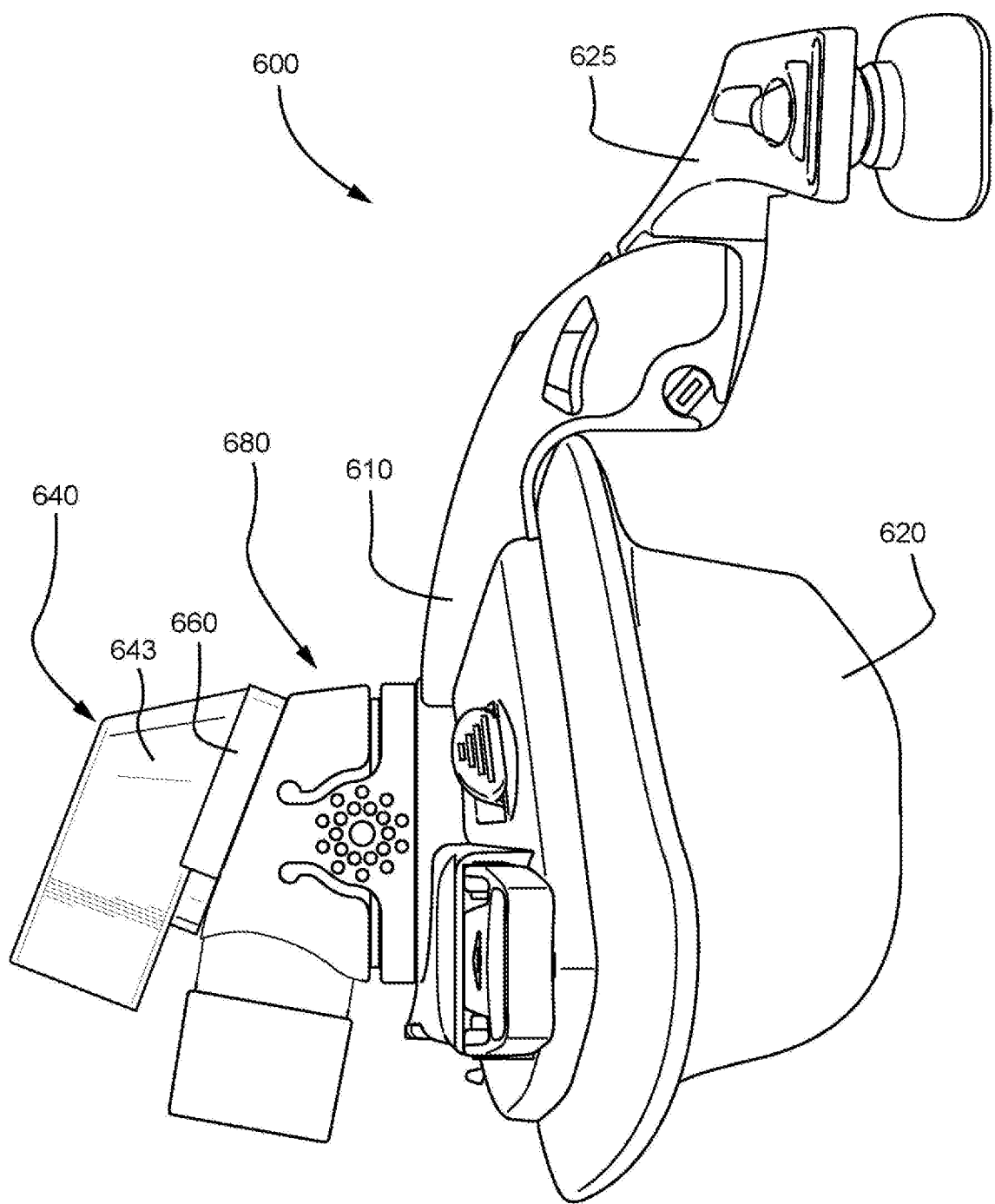
Figures 3, 4, 5, 6, 7:
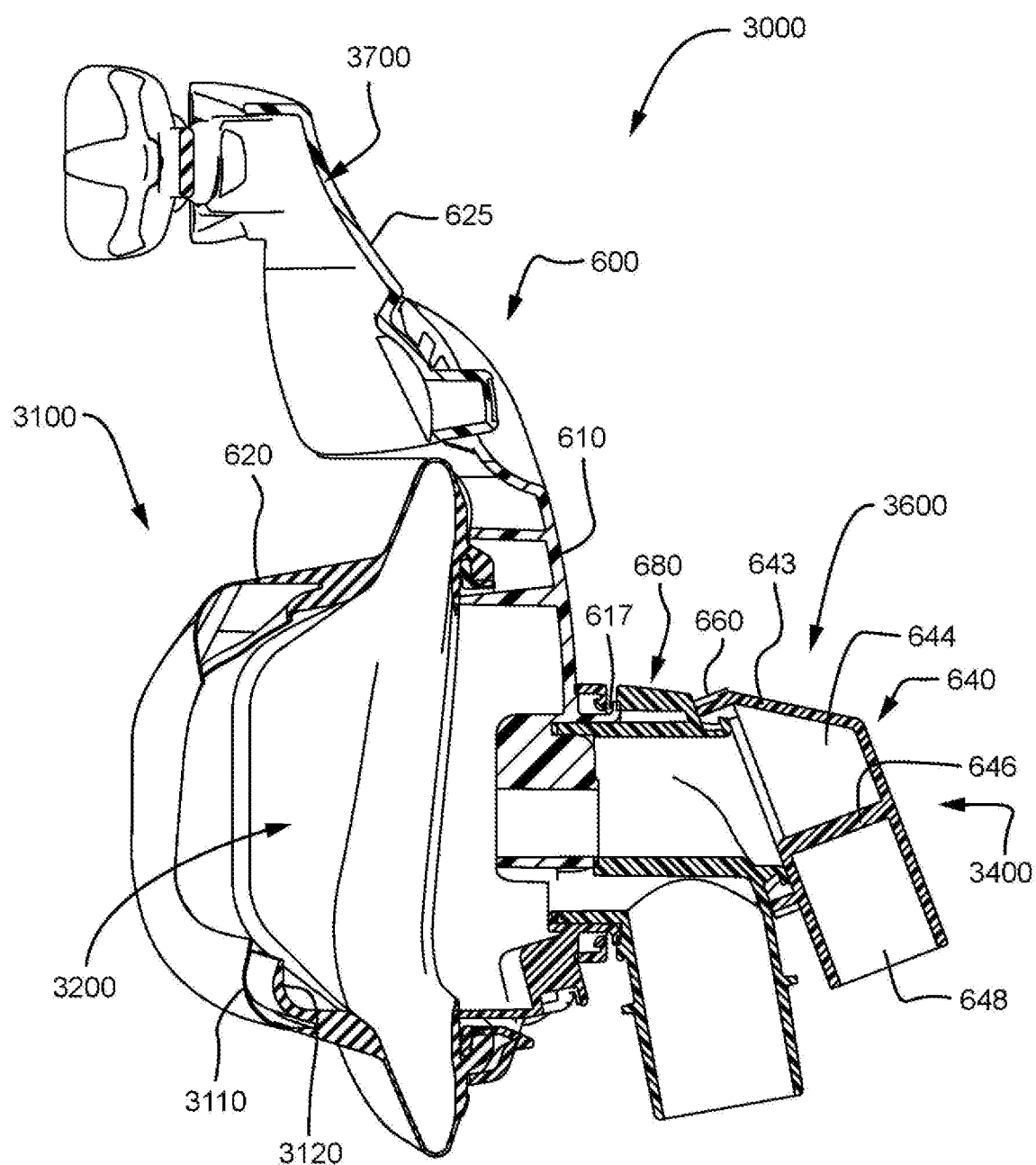
Figures 1, 3, 4, 5, 6, 7, 8:
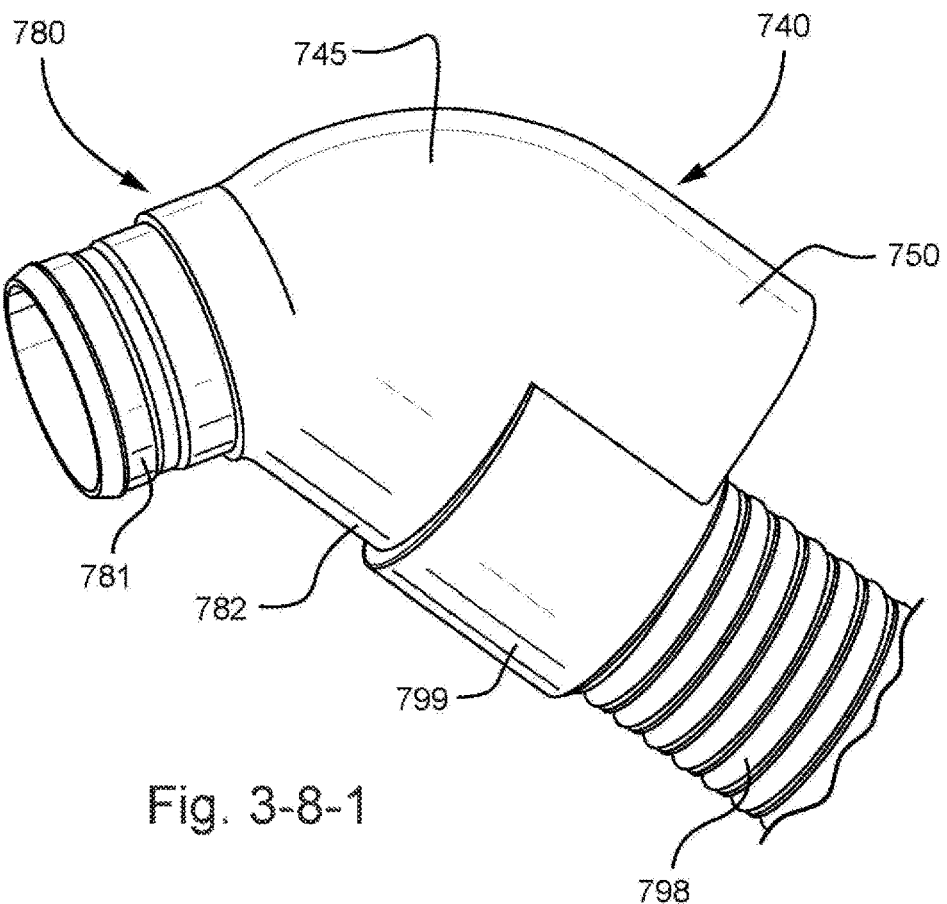
Figures 2, 3, 4, 5, 6, 7, 8:
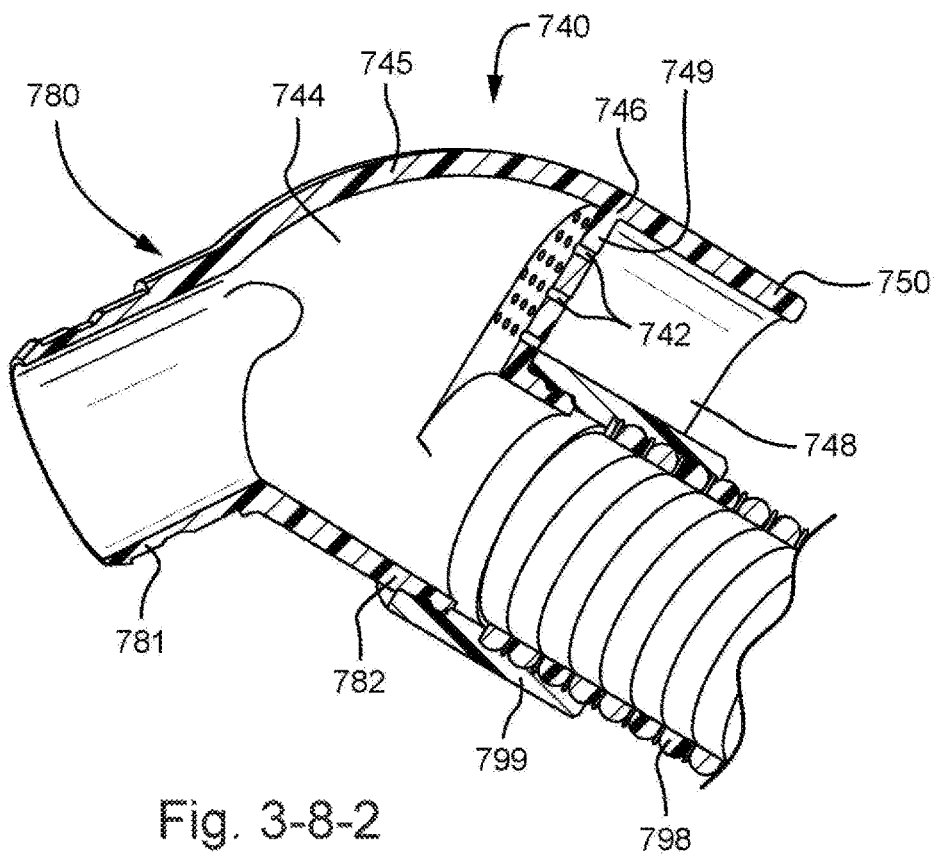
Figures 1, 3, 4, 5, 6, 7, 8, 9:
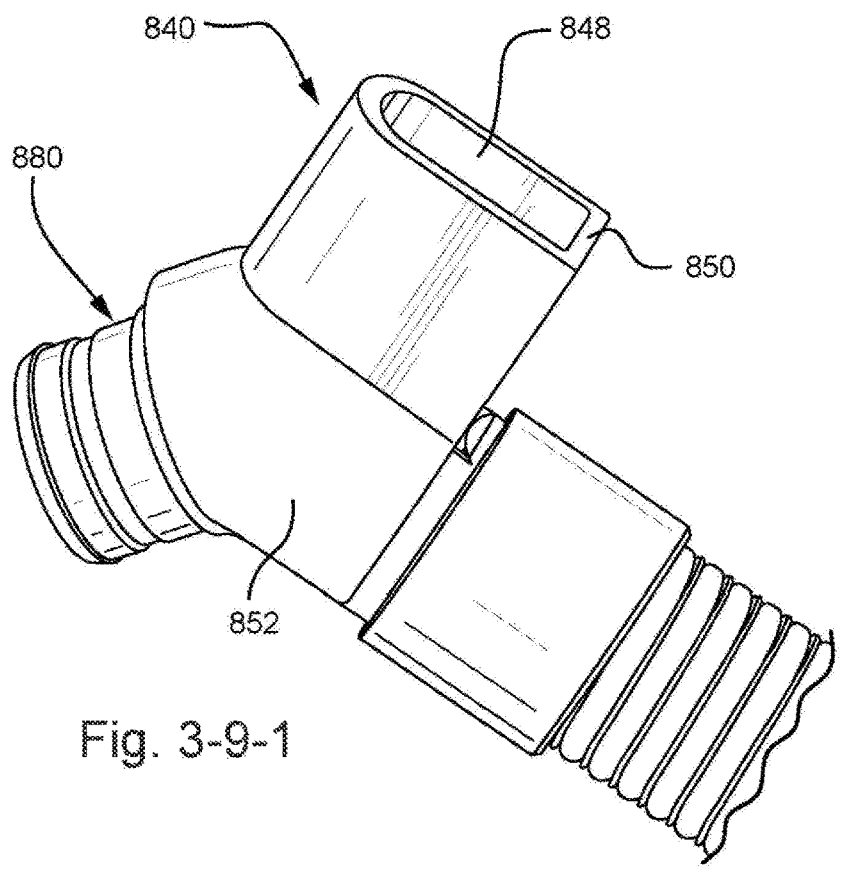
Figures 2, 3, 4, 5, 6, 7, 8, 9:
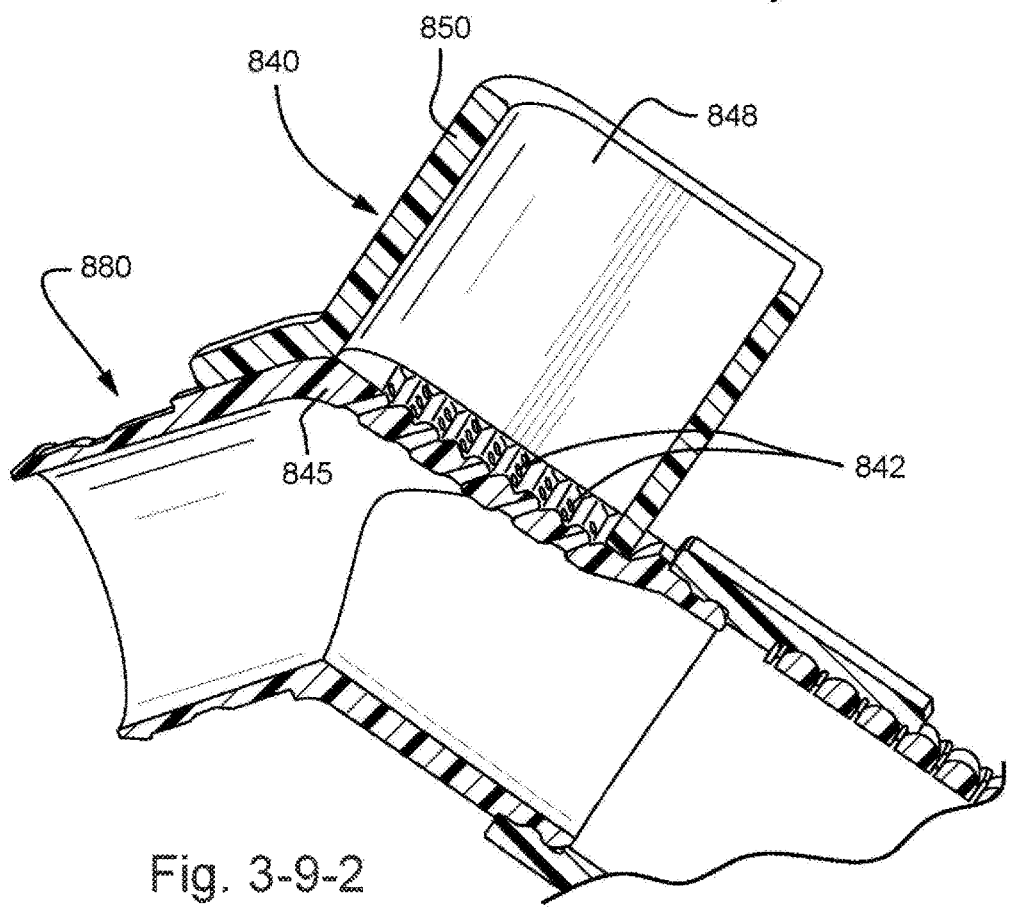
Figures 1, 3, 4, 5, 6, 7, 8, 9, 10:
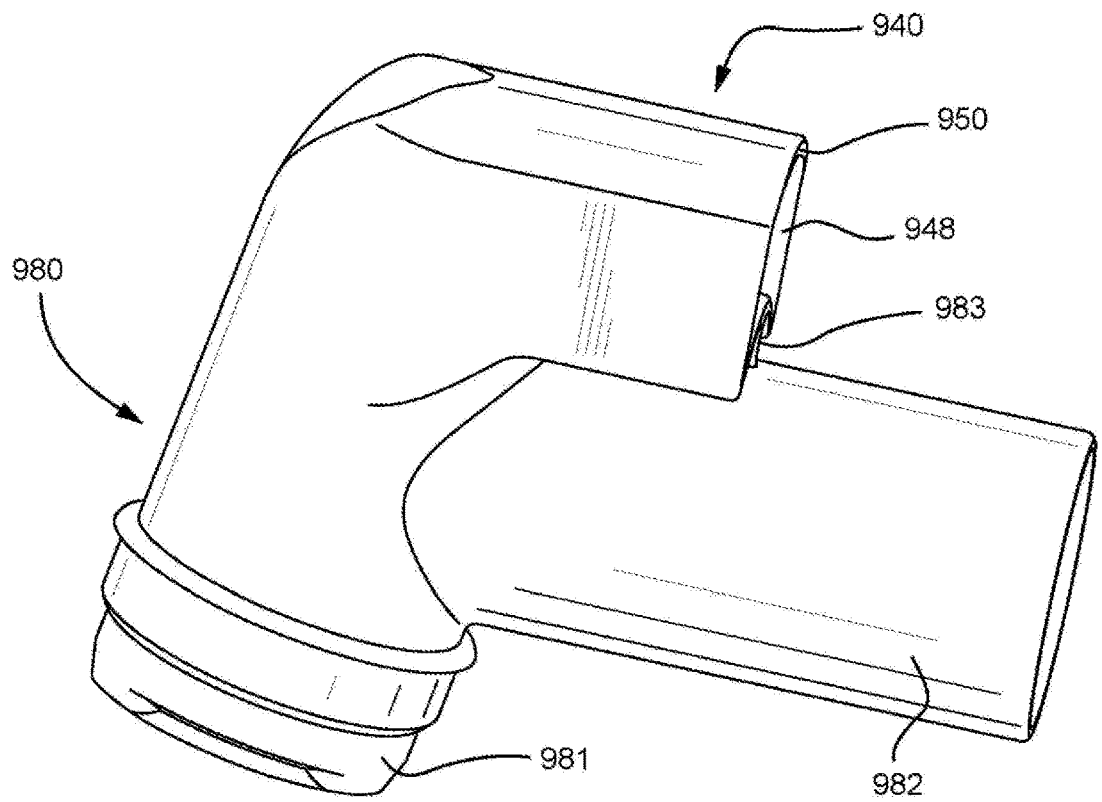
Figures 2, 3, 4, 5, 6, 7, 8, 9, 10:
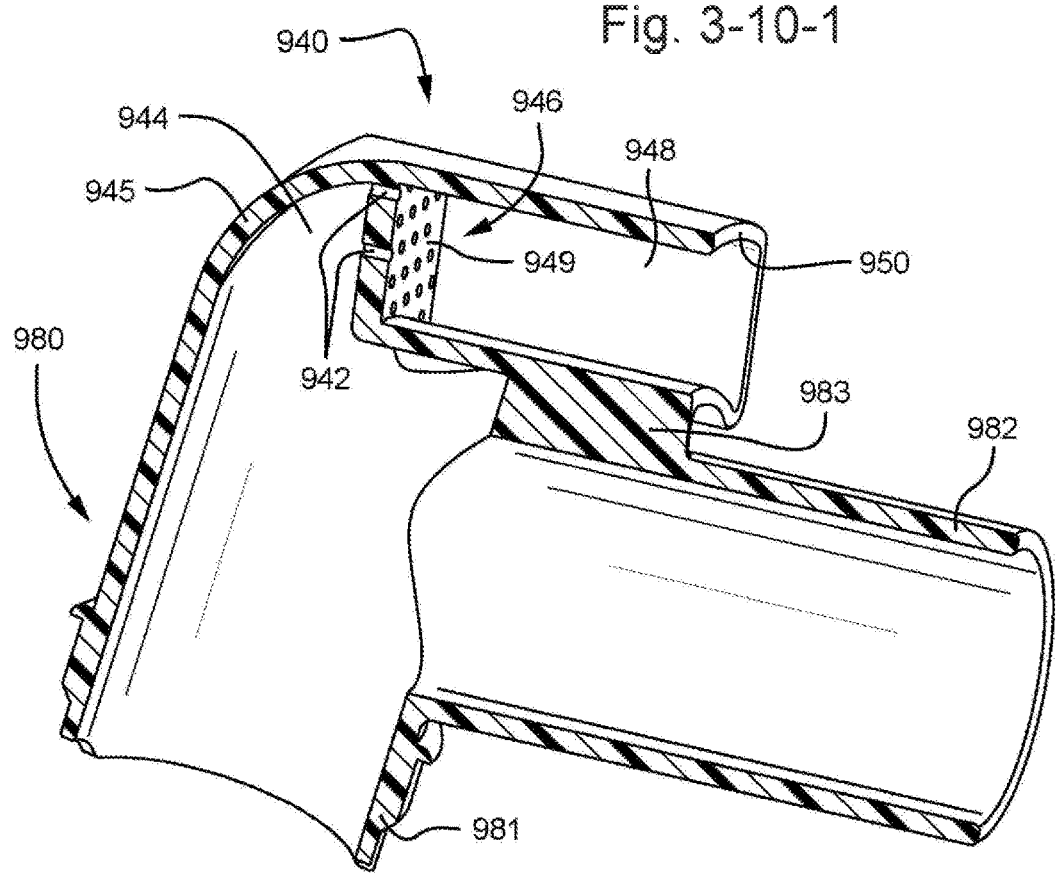
Figures 1, 3, 4, 5, 6, 7, 8, 9, 10, 11:
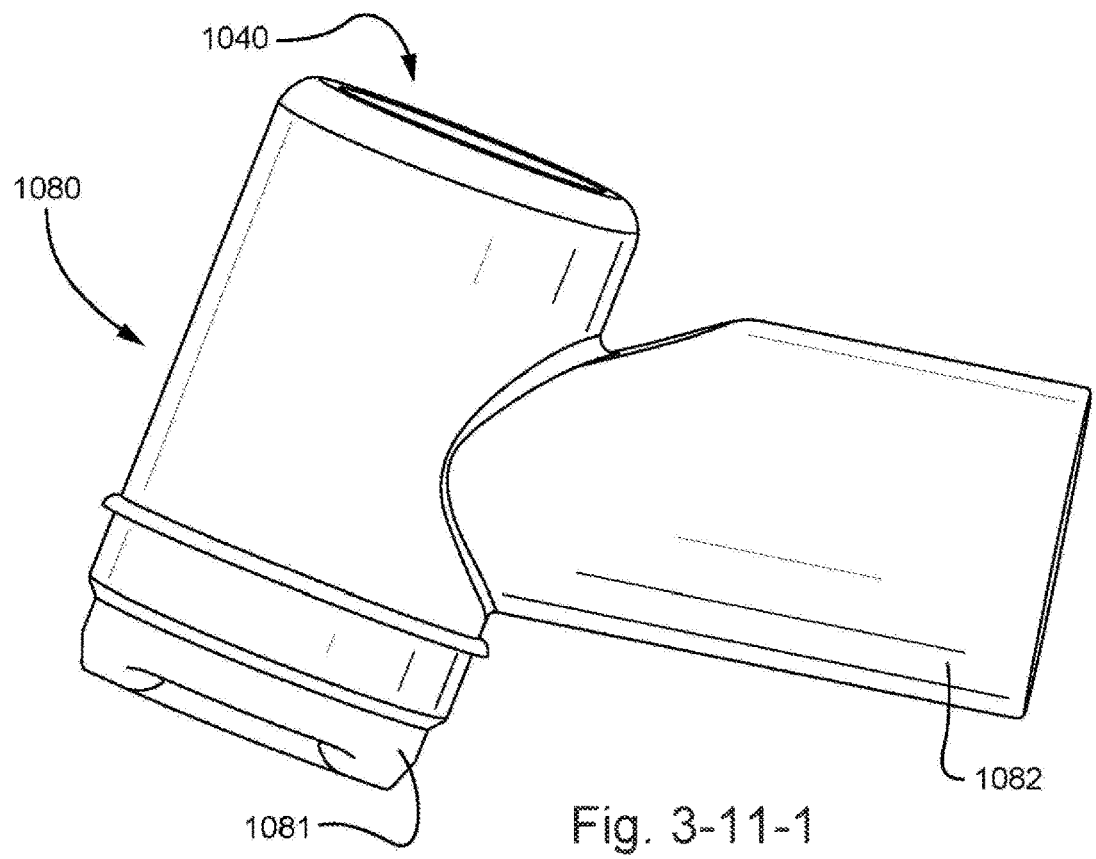
Figures 2, 3, 4, 5, 6, 7, 8, 9, 10, 11:
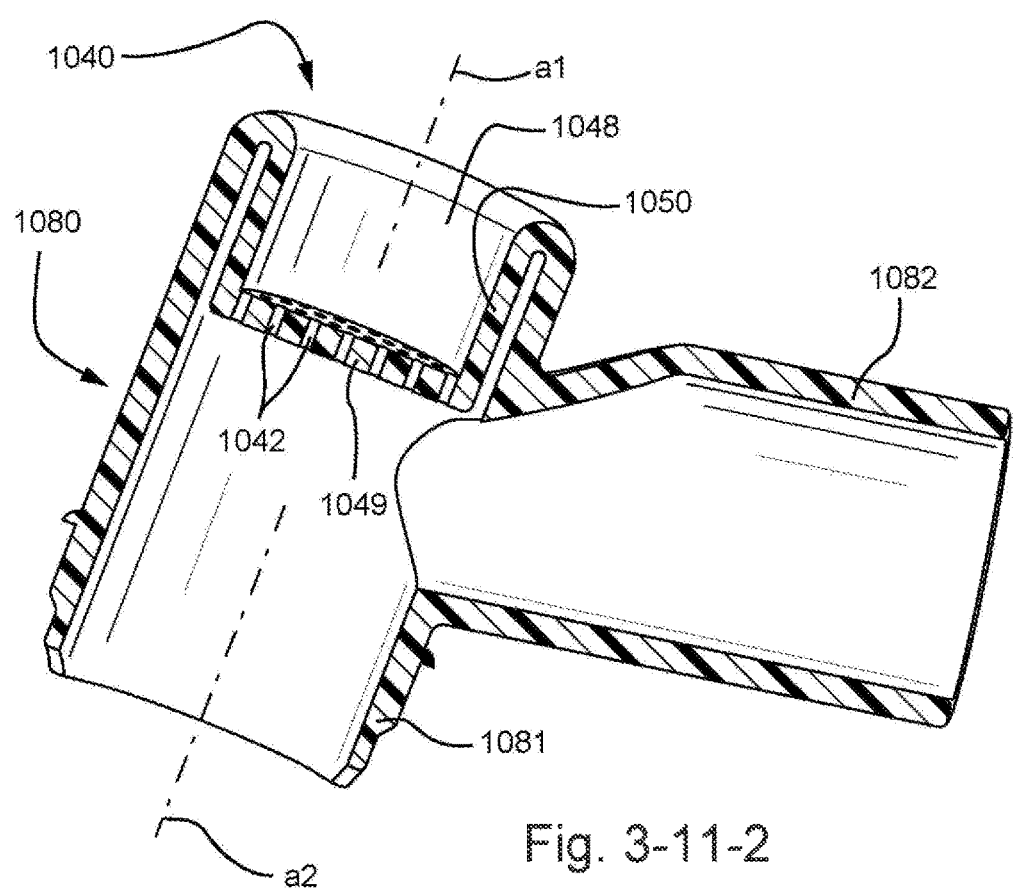
Figures 1, 3, 4, 5, 6, 7, 8, 9, 10, 11, 12:
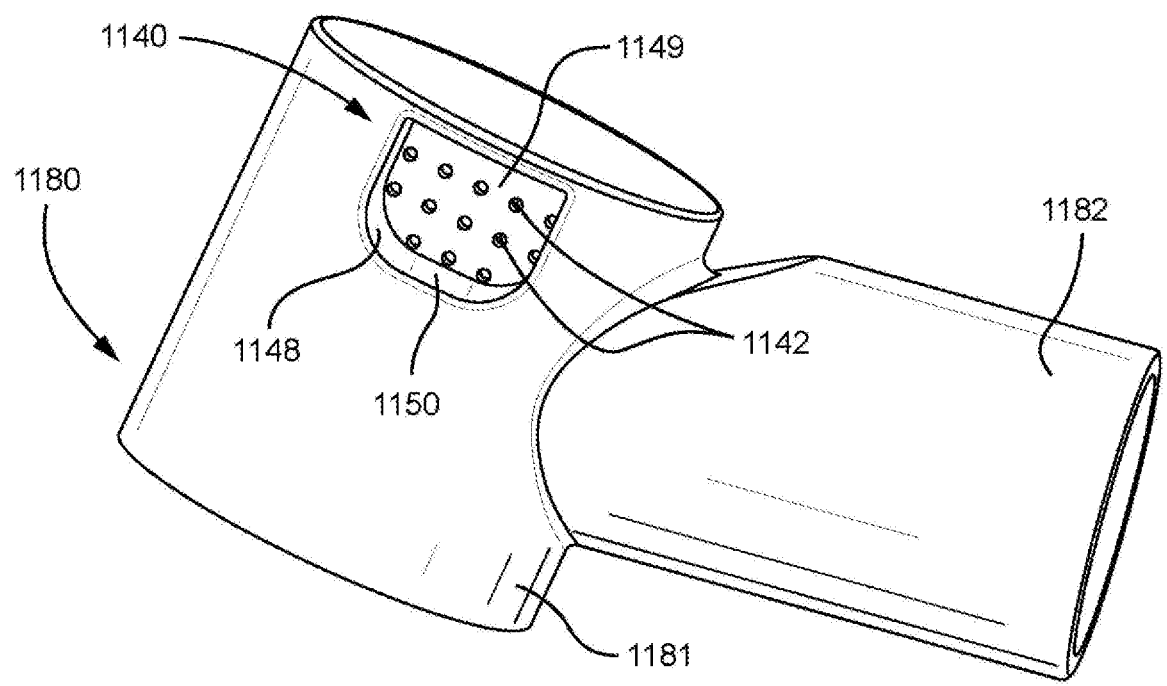
Figures 2, 3, 4, 5, 6, 7, 8, 9, 10, 11, 12:
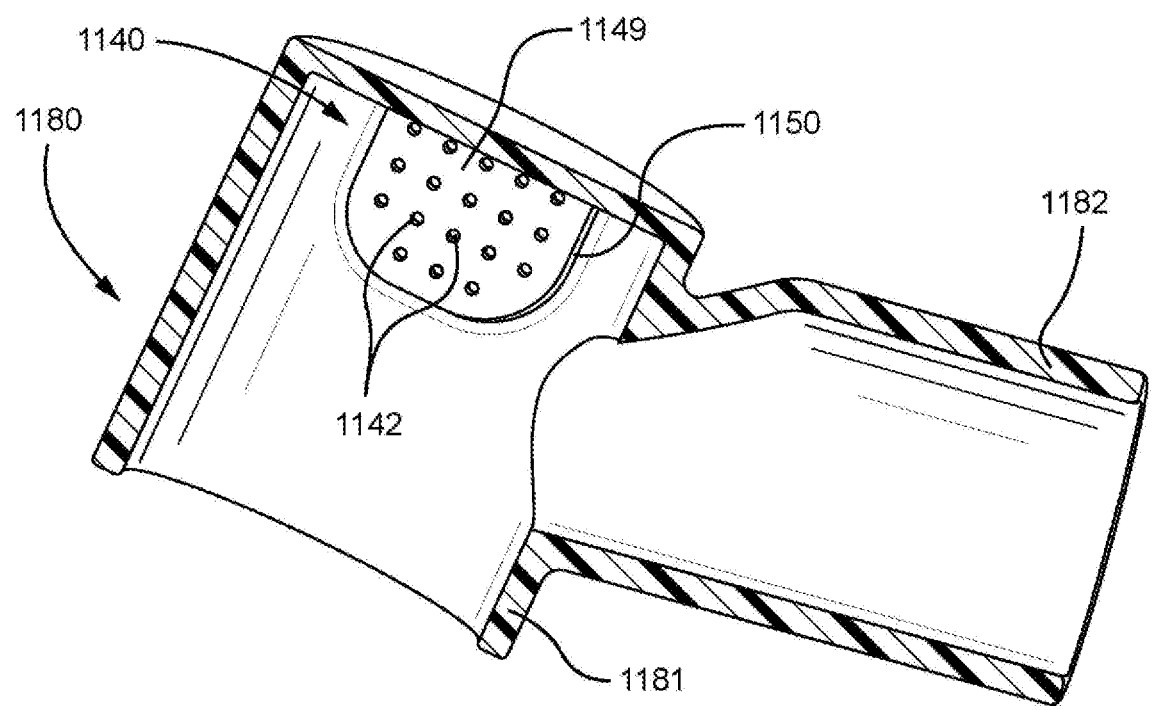
Figures 1, 3, 4, 5, 6, 7, 8, 9, 10, 11, 12, 13:
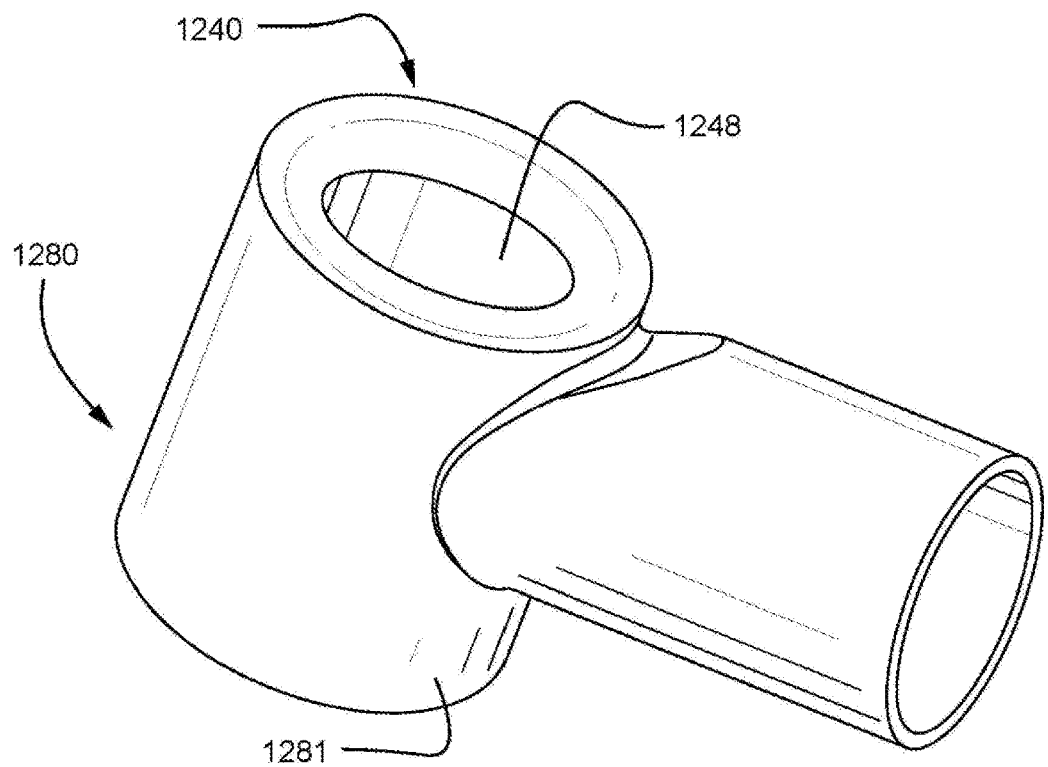
Figures 2, 3, 4, 5, 6, 7, 8, 9, 10, 11, 12, 13:
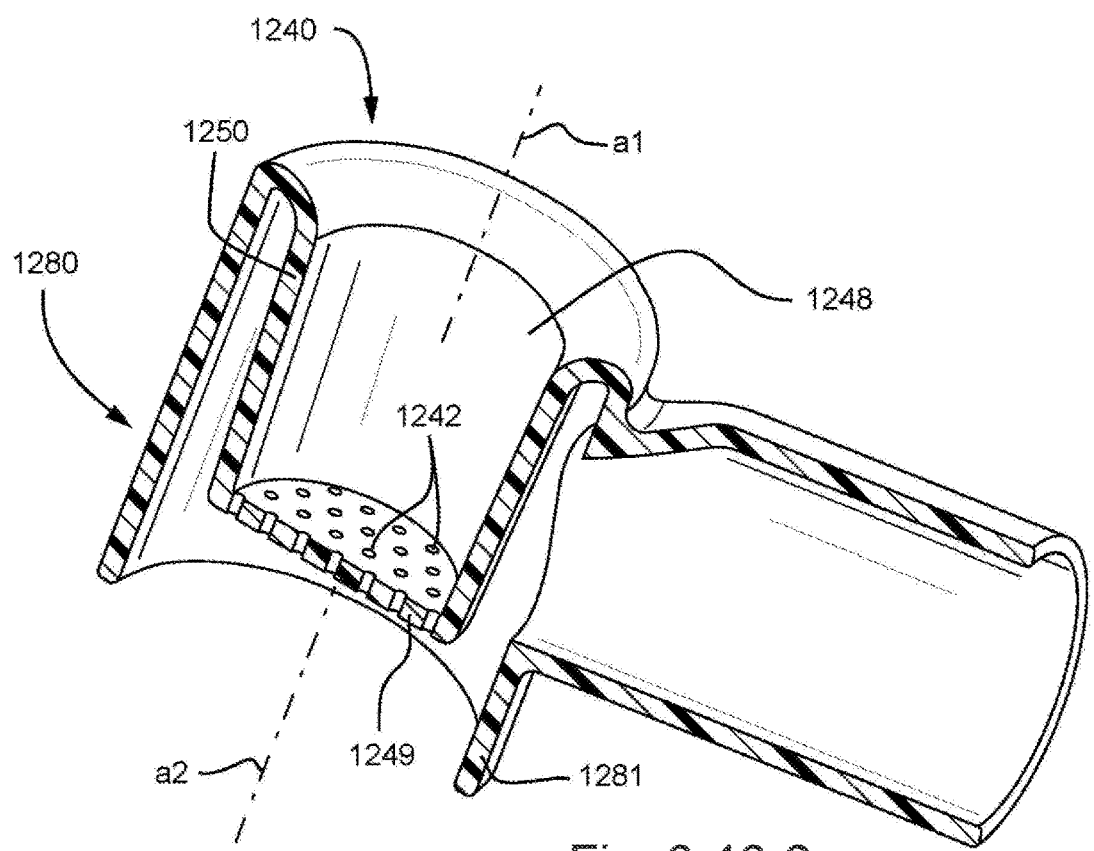

FIG. 3-4 shows a mask vent according to an example of the present technology.

FIGS. 3-5-1 to 3-5-7 show various views of an elbow assembly including a mask vent according to an example of the present technology.

FIGS. 3-6-1 to 3-6-2 show various views of an elbow assembly including a mask vent according to an example of the present technology.

FIGS. 3-6-3 to 3-6-9 show various views of the mask vent of FIGS. 3-6-1 to 3-6-2 removed from the elbow assembly.

FIGS. 3-7-1 to 3-7-5 show a mask system including the elbow assembly of FIGS. 3-6-1 to 3-6-2 according to an example of the present technology.

FIGS. 3-8-1 to 3-8-2 show various views of an elbow assembly including a mask vent according to an example of the present technology.

FIGS. 3-9-1 to 3-9-2 show various views of an elbow assembly including a mask vent according to an example of the present technology.

FIGS. 3-10-1 to 3-10-2 show various views of an elbow assembly including a mask vent according to an example of the present technology.

FIGS. 3-11-1 to 3-11-2 show various views of an elbow assembly including a mask vent according to an example of the present technology.

FIGS. 3-12-1 to 3-12-2 show various views of an elbow assembly including a mask vent according to an example of the present technology.

FIGS. 3-13-1 to 3-13-2 show various views of an elbow assembly including a mask vent according to an example of the present technology.

7.4 PAP Device

Figure 4A:
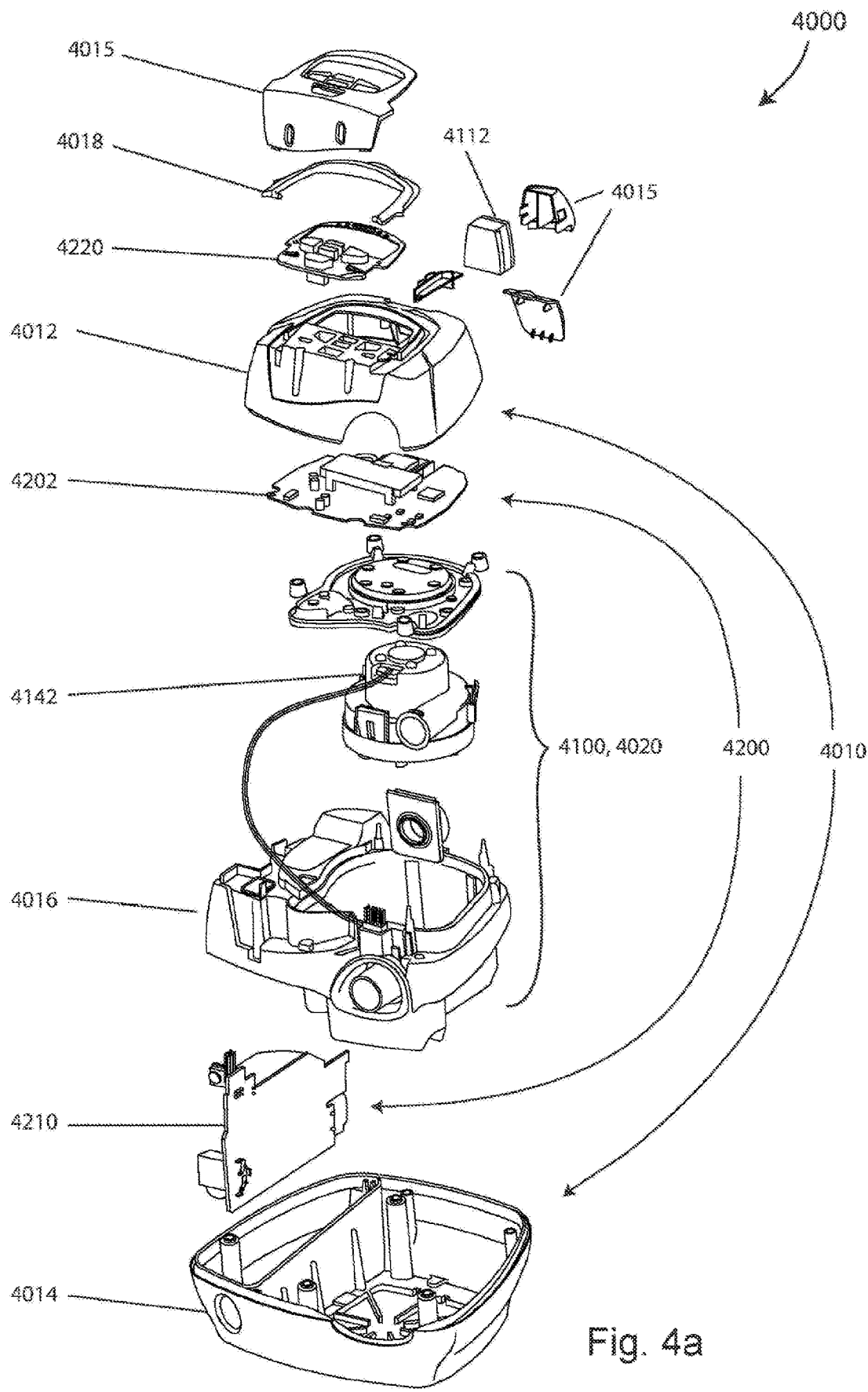

FIG. 4a shows a PAP device in accordance with one form of the present technology.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 TREATMENT SYSTEMS

In one form, the present technology comprises apparatus for treating a respiratory disorder. The apparatus may comprise a PAP device 4000 for supplying pressurised respiratory gas, such as air, to the patient 1000 via an air delivery tube leading to a patient interface 3000.

8.2 THERAPY

In one form, the present technology comprises a method for treating a respiratory disorder comprising the step of applying positive pressure to the entrance of the airways of a patient 1000.

8.2.1 Nasal CPAP for OSA

In one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

In certain embodiments of the present technology, mouth breathing is limited, restricted or prevented.

8.3 PATIENT INTERFACE 3000

A non-invasive patient interface 3000 in accordance with one aspect of the present technology comprises the following functional aspects: a seal-forming structure 3100, a plenum chamber 3200, a positioning and stabilising structure (e.g., headgear), and a connection port 3600 for connection to air circuit, e.g., see FIG. 3-7-5 for example. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120, e.g., see FIG. 3-7-5 for example. In an example, the sealing flange 3110 comprises a relatively thin member with a thickness of less than about 1 mm, for example about 0.25 mm to about 0.45 mm, that extends around the perimeter of the plenum chamber 3200. Support flange 3120 may be relatively thicker than the sealing flange 3110. The support flange 3120 is disposed between the sealing flange 3110 and the marginal edge of the plenum chamber 3200, and extends at least part of the way around the perimeter. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In another form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk; and a flexible region on the underside of the frusto-cone connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

8.3.2 Plenum Chamber 3200

The plenum chamber 3200 may have a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

8.3.3 Positioning and Stabilising Structure

The seal-forming structure 3100 of the patient interface 3000 of the present technology may be held in sealing position in use by the positioning and stabilising structure.

8.3.4 Vent 3400

In one form, the patient interface 3000 may include a vent 3400 constructed and arranged to allow for the washout of exhaled carbon dioxide, e.g., see FIG. 3-7-5.

One form of vent 3400 in accordance with the present technology comprises a plurality of holes, for example, about 2 to about 40 holes, about 5 to about 20 holes, about 20 to about 80 holes, about 40 to about 60 holes, or about 45 to about 55 holes. In an alternative implementation, the vent 3400 can comprise a woven mesh structure comprising numerous microscopic holes.

The vent 3400 may be located in the plenum chamber. Alternatively, the vent may be located in a decoupling structure, e.g. a swivel.

FIG. 3-1 shows a patient interface in accordance with one form of the present technology including a mask system or mask 100 including a rigid or semi-rigid portion 110 (often referred to as a shell or frame) and a soft, patient contacting portion 120 adapted to form a seal with the patient's nose and/or mouth (often referred to as the seal forming structure, cushion, or nasal prong arrangement). An elbow assembly may be provided to the frame and adapted to be connected to an air delivery tube that delivers breathable gas to the patient. However, it should be appreciated that other mask arrangements are possible, e.g., not rigid (e.g., constructed of cloth).

One or more gas washout vents or vent arrangements 140 are provided to the mask or associated conduit to discharge exhaled gas from the mask to atmosphere. In examples, the one or more vents may be provided to a mask component of the mask, i.e., to the frame and/or to the elbow assembly of the mask. One or more vents in the associated conduit are also possible.

It should be appreciated that each vent may be adapted for use with any suitable interface type, e.g., nasal masks, full-face masks, nose and mouth masks, nasal prongs, pillows, nozzles, cannulae, etc.

The vent arrangements in accordance with examples of the present technology are structured to disperse or diffuse the exhaust vent flow. Increased dispersion or diffusion of exhaust vent flow reduces disturbing or unfavourable effects of vent airflow, e.g., air jetting onto bed clothes/pillows and bed partners, noise.

In examples, one or more side walls are provided around the washout vents or holes to surround or enclose the vent outlet or vent exit of the vent holes and reduce the unfavourable effects of vent airflow.

In an example, venting flow at 12 $cmH_2O$ pressure is about 40 L/m, and air velocity at each vent opening is about 45 m/s about (162 km/h). Such high velocity vent airflow will cause vent airflow from all the adjacent vent holes to converge with one another and pull in additional air surrounding the venting area into the converged stream due to the Venturi effect. The amount of air pulled into the converged stream can be more than 10 times larger than the original flow in some examples. To prevent or at least reduce additional air from being pulled into the vent airflow, a side wall is provided around the venting area according to examples of the present technology.

In an example, the side wall reduces negative pressure along the surface adjacent the vent outlet which reduces air being pulled into the vent stream. This allows greater dispersion or diffusion of the vent airflow adjacent the vent outlet and at least reduces convergence of the air stream to reduce air velocity downstream from the vent outlet. In an example, the air velocity downstream from the venting area (e.g., about 300 mm downstream from the venting area) provided with a side wall may be at least ½ or less (e.g., ⅓) of the air velocity downstream from the venting area with no side wall. As a result, venting noise (e.g., sound power (dB)) is reduced, as is disruption to any bed-partner 1100 of the patient 1000. In effect, the venting flow has been spread over a wider area, achieving a more even or uniform flow profile across the walled area, thereby decreasing its velocity. The amount of reduction of downstream air velocity increases with the height of the side wall up to the limit which is reached with uniform flow.

The greater the density of vent holes, the smaller the holes may be made while maintaining the same venting flow rate. It may be shown that a greater density of smaller holes improves the amount of diffusion for the same height of surrounding side wall. In other words, as the density of vent holes increases, the side wall height may be reduced while preserving the same reduction in downstream air velocity at a given distance from the vent. In one example, 36 tapered vent holes of 0.75 mm diameter are disposed on a uniform hexagonal grid with inter-hole spacing of 2.5 mm. In this example, the side wall height is 10 mm.

In an example, as shown in FIG. 3-1, the mask vent 140 is provided to the mask frame 110 of the mask system 100. In the illustrated example, the mask system includes the mask frame 110, the cushion 120 provided to the frame and adapted to form a seal with the patient's nose and mouth, and a shroud 130 provided to the frame and structured to attach headgear to the mask system. The lower portion of the frame includes an opening 112 adapted to receive or otherwise communicate with an elbow assembly, and the upper portion of the frame includes the mask vent 140 for gas washout. As illustrated, the bottom end of the shroud 130 includes an opening 132 to accommodate the elbow assembly and the top end of the shroud 130 includes an opening 134 to accommodate the mask vent 140. Further examples and details of such mask system are disclosed in International Publication No. WO 2009/108995, which is incorporated herein by reference in its entirety. However, it should be appreciated that the mask vent 140 may be adapted for use with other suitable interface types.

As illustrated, the mask vent 140 includes a venting area 141 having a plurality of vent holes 142. Each vent hole extends through a thickness of the mask frame and each includes a vent exit. The mask vent 140 includes a continuous side wall 150 provided to the mask frame structured to surround the plurality of vent exits of the vent holes 142. In an alternative example, the side wall may at least partly surround one or more of the vent holes.

The term "side wall" should be understood to include not only structures that project outwards from the mask component, such as the side wall 150, but also structures that project inwards from the mask component, such as a wall surrounding a recess in the mask component. In an example of such a configuration, as described below, the mask vent may be recessed within an interior of the mask, i.e., the side wall of the vent supports the venting area within an interior of the mask.

In an alternative example, the side wall may include a hood to at least partly surround or enclose one or more of the vent holes.

In the illustrated example, the side wall 150 extends in the direction of the vent airflow (e.g., perpendicular to the exterior surface 115 of the mask frame 110 and/or perpendicular to a longitudinal axis of each vent hole 142). In alternative examples, the side wall may be angled with respect to the exterior surface of the mask frame and/or the longitudinal axis of each vent hole.

In the illustrated example, the side wall 150 includes a uniform or constant height along its perimeter, e.g., side wall includes substantially the same height from its connection to the frame to its free end. However, in an alternative example, the side wall may include one or more portions with different heights along its perimeter.

In the illustrated example, the side wall 150 includes a uniform or constant thickness along its entire perimeter and from its connection to the frame to its free end. However, in an alternative example, the thickness of the side wall may be tapered along its height, e.g., tapered from its connection to the frame to its free end. Also, in an alternative example, the side wall may include different thicknesses along its perimeter.

In the illustrated example, the vent holes 142 are arranged in columns. e.g., to allow more holes to be fitted into a smaller space. As illustrated, the vent arrangement includes a center column including five holes which is flanked by inner intermediate columns each including five holes which is flanked by outer intermediate columns each including four holes which is flanked by outside columns each including four holes. The holes in the outside columns are aligned with holes in the inner intermediate columns, which are offset from holes in the center column and outer intermediate column, forming a hexagonal grid arrangement. It should be appreciated that each column may include any suitable number of holes, and the columns may be arranged in other suitable manners with respect to one another.

In the illustrated example, the vent holes 142 are arranged to provide a venting area 141 with a generally oblong, ovoid, or oval shape. As illustrated, the side wall 150 is continuous and is structured to surround the entire venting area 141, e.g., side wall includes generally similar shape to the venting area, e.g., generally oblong, ovoid, or oval shaped side wall. However, in alternative examples, the side wall may include a different shape than the venting area. Also, the side wall may be structured to only surround one or more portions of the venting area. In addition, it should be appreciated that the venting area and side wall may have other suitable shapes, e.g., depending on mask configuration, venting requirements, etc.

For example, FIGS. 3-2 to 3-4 illustrate alternative side wall arrangements. In FIG. 3-2, the side wall 250 includes a hexagonal shape that surrounds the venting area 241 with vent holes 242. In FIG. 3-3, the side wall 350 includes a circular shape that surrounds the venting area 341 with vent holes 342. In FIG. 3-4, the side wall 450 includes a circular shape that surrounds the venting area 441 with vent holes 442, and a plurality of truncated interior walls or ribs 445 are provided within the side wall 450 and extend at least partially through the venting area 441. As illustrated, the interior walls are arranged in a radial manner from an axis of the circular side wall. However, it should be appreciated that the interior walls or ribs may have other suitable shapes, e.g., arcuate or non-linear shape, and may be arranged within the venting area in other suitable manners.

Each vent hole may have a generally part conic shape, including opposed walls that converge from a larger diameter to a smaller diameter, as viewed in the direction of exhausted gas. Alternatively, each vent hole may have a generally cylindrical shape with a substantially constant diameter along its length.

In an alternative example, the mask vent may be provided to the elbow assembly of the mask system. For example, the mask vent may be integrated or integrally formed in one piece with the elbow assembly. Alternatively, the mask vent may be retrofit to an existing elbow assembly, e.g., replace an original or existing mask vent on an elbow assembly.

For example, FIGS. 3-5-1 to 3-5-7 show the mask vent 540 integrally formed (e.g., molded) in one piece with the elbow assembly 580. The arrangement provides a single piece elbow assembly with removable parts.

As illustrated, the elbow assembly 580 includes a first end 581 structured to releasably engage with an opening in a mask frame and a second end 582 structured to releasably engage with an air delivery tube. In the illustrated example, the first end 581 includes a flexible quick release mechanism including a T-shaped collar 583 structured to releasably engage a flange surrounding the opening in the mask frame with a snap-fit. Further examples and details of such quick release mechanism are disclosed in U.S. Pat. No. 6,907,882, which is incorporated herein by reference in its entirety. However, it should be appreciated that the elbow assembly may be connected or otherwise communicated with the opening in the mask frame in other suitable manners.

A baffle 584 is provided within the interior portion of the elbow assembly and separates the intake port 590 and the exhaust port 592, e.g., see FIGS. 3-5-6 and 3-5-7. The mask vent 540 is provided at the outlet of the exhaust port 592. In this manner, exhalation gases from an interior of the mask can flow through exhaust port 592 of the elbow assembly 580, through the mask vent 540, and to the atmosphere.

As illustrated, the mask vent 540 includes an inlet portion 544 to receive gas from the outlet of the exhaust port 592 of the elbow assembly, a vent portion 546 including the plurality of vent holes 542, and an outlet portion 548 to receive gas from the outlets of the vent holes 542. In the example, the inlet portion 544 includes an arcuate or otherwise angled side wall 545 to guide exhaust gas from the outlet towards the vent and outlet portions. In the illustrated example, as best shown in FIG. 3-5-7, the axes of the vent holes 542 and a longitudinal axis a1 of the outlet portion 548 are oriented to direct exhaust gas in a direction that is slightly offset or possibly parallel to a longitudinal axis a2 of the second end 582 of the elbow assembly (e.g., axes oriented about 0-45° from the axis of the second end), e.g., to ensure gas is vented in a direction away from the mask system and the patient. In the example, the outlet portion 548 provides a continuous, side wall 550 around the vent portion and vent holes thereof to enhance dispersion or diffusion of exhaust vent flow as described above.

In the illustrated example, the vent holes 542 are provided through an interior wall 549 of the mask vent 540 and arranged in columns of five vent holes, and the side wall 550 includes a generally rectangular shape that surrounds the vent holes and extends in the direction of the vent airflow. However, as noted above, it should be appreciated that the vent holes and side wall may have other suitable arrangements.

FIGS. 3-6-1 to 3-6-9 show an elbow assembly 680 and mask vent 640 according to another example of the present technology. In contrast to the example shown in FIGS. 3-5-1 to 3-5-7, the mask vent 640 is provided as a vent cap that is formed separately from the elbow assembly 680 and attached thereto. In an example, the vent cap may be retrofit to an existing elbow assembly, e.g., vent cap replaces elastomeric vent cover on elbow assembly disclosed in U.S. Pat. No. 6,907,882 for example.

As illustrated in FIG. 3-6-2, the elbow assembly 680 includes a flange 686 provided at a distal end of an annular wall 687 surrounding the outlet of the exhaust port 692. The vent cap 640 is structured to releasably engage the flange 686, e.g., with a snap-fit, to connect the vent cap 640 to the elbow assembly 680. Remaining aspects of the elbow assembly 680, e.g., first end 681 with flexible quick release mechanism, second end 682, baffle 684 separating intake port 690 and exhaust port 692 is similar to elbow assembly 580 described above.

The vent cap 640 includes a main body 643 providing an inlet portion 644 with arcuate or angled side wall 645 to guide exhaust gas from the outlet of the elbow assembly towards the vent, a vent portion 646 including interior wall 649 with the plurality of vent holes 642, and an outlet portion 648 including side wall 650 to diffuse vent flow as described above.

A support wall 647 is provided to the inlet portion 644 along its inlet opening. As illustrated, the support wall 647 includes a non-continuous structure, e.g., first and second wall portions 647.1 and 647.2, e.g., see FIGS. 3-6-3 and 3-6-6. However, it should be appreciated that the support wall may have other suitable structures, e.g., continuous wall structure.

An engagement or seal ring 660. e.g., constructed of a more flexible material than the main body 643, is provided to the support wall 647. The engagement ring 660 includes grooves 661 through its thickness that are adapted to receive respective wall portions 647.1 and 647.2 of the support wall 647 (e.g., see FIGS. 3-6-2, 3-6-3, 3-6-6, and 3-6-9) so as to attach the engagement ring to the support wall. The engagement ring 660 may be formed separately and attached to the support wall 647, or the engagement ring 660 may be integrally formed along with the main body 643 and support wall thereof, e.g., co-molded.

As best shown in FIG. 3-6-9, the engagement ring 660 includes an annular groove 662 along its inside surface. The inside surface may be ramped or tapered along it entry opening 664 to facilitate engagement and alignment of the engagement ring with the flange on the elbow assembly. FIG. 3-6-2 shows the vent cap 640 assembled to the elbow assembly 680, with the flange 686 on the elbow assembly 680 engaged within the groove 662 of the engagement ring 660 of the vent cap 640.

FIGS. 3-7-1 to 3-7-5 show the elbow assembly 680 and mask vent 640 of FIGS. 3-6-1 to 3-6-9 provided to a mask system 600 according to an example of the present technology. The mask system 600 includes a mask frame 610, cushion 620, and forehead support 625, further examples and details of such mask system being disclosed in U.S. Pat. No. 7,523,754, which is incorporated herein by reference in its entirety. However, it should be appreciated that the elbow assembly and mask vent thereof may be adapted for use with other suitable interface types. The elbow assembly 680 is structured to releasably engage a flange 617 surrounding the opening in the mask frame 610 of the mask system 600, e.g., with a snap-fit.

FIGS. 3-8-1 and 3-8-2 show an elbow assembly 780 and mask vent 740 according to another example of the present technology. In this example, the mask vent is integrally formed (e.g., molded) in one piece with the elbow assembly.

As illustrated, the elbow assembly 780 includes a first end 781 structured to releasably engage with an opening in a mask frame and a second end 782 structured to releasably engage with an air delivery tube 798. In this example, the interior of the elbow assembly is provided without a baffle. The mask vent provides inlet portion 744 with arcuate or angled side wall 745 to guide exhaust gas exiting from the first end 781 towards the vent, vent portion 746 including interior wall 749 with the plurality of vent holes 742, and outlet portion 748 including side wall 750 to diffuse vent flow and ensure gas is vented in a direction away from the mask system and the patient 1000 as described above. As illustrated, the side wall 750 includes a semi-circular configuration that overlaps with the cuff 799 of the air delivery tube 798 to establish the outlet portion 748 that surrounds the vent holes 742.

FIGS. 3-9-1 and 3-9-2 show an elbow assembly 880 and mask vent 840 according to another example of the present technology. In this example, the vent holes 842 are provided to side wall 845 of the elbow assembly 880, and the outlet portion 848 including side wall 850 that surrounds the vent holes 842 is provided as a separate cover piece that is formed separately and attached to the side wall 845 of the elbow assembly 880, e.g., with a snap fit. In an example, the cover piece is provided as a retrofit to an existing elbow assembly. However, it should be appreciated that the cover piece may be integrated or integrally formed in one-piece, e.g., co-molded, with the elbow assembly.

In the illustrated example, the cover piece includes semi-circular arms or wings 852 extending from lateral sides of the side wall 850. The arms or wings 852 are resiliently flexible and structured to wrap around the perimeter of the elbow assembly to secure the cover piece in position.

FIGS. 3-10-1 and 3-10-2 show an elbow assembly 980 and mask vent 940 according to another example of the present technology. In this example, the mask vent is integrally formed (e.g., molded) in one piece with the elbow assembly.

As illustrated, the elbow assembly 980 includes a first end 981 structured to releasably engage with an opening in a mask frame and a second end 982 structured to releasably engage with an air delivery tube. In this example, the interior of the elbow assembly is provided without a baffle. The mask vent provides inlet portion 944 with arcuate or angled side wall 945 to guide exhaust gas exiting from the first end 981 towards the vent, vent portion 946 including interior wall 949 with the plurality of vent holes 942, and outlet portion 948 including side wall 950 to diffuse vent flow and ensure gas is vented in a direction away from the mask system and the patient 1000 as described above. As illustrated, the side wall 950 is spaced from the second end 982 by support wall 983.

FIGS. 3-11-1 and 3-11-2 show an elbow assembly 1080 and mask vent 1040 according to another example of the present technology. In this example, the mask vent is integrally formed (e.g., molded) in one piece with the elbow assembly.

As illustrated, the elbow assembly 1080 includes a first end 1081 structured to releasably engage with an opening in a mask frame and a second end 1082 structured to releasably engage with an air delivery tube. In this example, the axes of the vent holes 1042 and a longitudinal axis a1 of the outlet portion 1048 are aligned or parallel with a longitudinal axis a2 of the first end 1081 of the elbow assembly. As illustrated, the side wall 1050 of the outlet portion 1048 supports the vent wall 1049 with the plurality of vent holes 1042 within an interior of the elbow assembly, and the side wall 1050 overlaps with side walls of the elbow assembly 1080. In an alternative implementation, the side wall 1050 coincides with the side walls of the elbow assembly 1080. In other words, the side walls of the elbow assembly 1080 also serve as the side wall 1050 of the outlet portion 1048.

FIGS. 3-12-1 and 3-12-2 show an elbow assembly 1180 and mask vent 1140 according to another example of the present technology. In this example, the mask vent is integrally formed (e.g., molded) in one piece with the elbow assembly.

As illustrated, the elbow assembly 1180 includes a first end 1181 structured to releasably engage with an opening in a mask frame and a second end 1182 structured to releasably engage with an air delivery tube. In this example, the mask vent 1140 is provided on lateral sides of the elbow assembly. Each mask vent 1140 includes a recessed configuration with the side wall 1150 of the outlet portion 1148 supporting the vent wall 1149 with the plurality of vent holes 1142 within an interior of the elbow assembly.

FIGS. 3-13-1 and 3-13-2 show an elbow assembly 1280 and mask vent 1240 according to another example of the present technology. In this example, the mask vent is integrally formed (e.g., molded) in one piece with the elbow assembly.

Similar to the example of FIGS. 3-11-1 and 3-11-2, the axes of the vent holes 1242 and a longitudinal axis a1 of the outlet portion 1248 are aligned or parallel with a longitudinal axis a2 of the first end 1281 of the elbow assembly, and the side wall 1250 supports the vent wall 1249 with the plurality of vent holes 1242 within an interior of the elbow assembly. In this example, the side wall 1250 extends further into the interior of the elbow assembly so as to define at least a portion of a baffle wall that separates the intake port and the exhaust port. As a further benefit of this extension, during inspiration, the Venturi effect results in a relatively low pressure zone around the venting holes and thus reduces the venting flow through the vent 1240 during inspiration. Conversely, during expiration, the Venturi effect results in enhanced gas washout.

8.3.5 Decoupling Structure(s)

In one form the patient interface 3000 includes at least one decoupling structure, for example a swivel or a ball and socket.

8.3.6 Connection Port 3600

Connection port 3600 allows for connection to the air circuit.

8.3.7 Forehead Support 3700

In one form, the patient interface 3000 includes a forehead support 3700, e.g. see FIG. 3-7-5.

8.3.8 Anti-Asphyxia Valve

In one form, the patient interface 3000 includes an anti-asphyxia valve.

8.3.9 Ports

In one form of the present technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

8.4 PAP DEVICE 4000

A preferred PAP device 4000 in accordance with one aspect of the present technology comprises mechanical and pneumatic components 4100, electrical components 4200 and is programmed to execute one or more algorithms. An exemplary PAP device has an external housing 4010, formed in two parts, an upper portion 4012 of the external housing 4010, and a lower portion 4014 of the external housing 4010. In alternative forms, the external housing 4010 may include one or more panel(s) 4015. The PAP device 4000 may comprise a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may comprise an inlet air filter 4112, an inlet muffler, a controllable pressure device capable of supplying air at positive pressure (e.g., a blower 4142), and an outlet muffler. The pneumatic block 4020 may comprise a portion of the pneumatic path that is located within the external housing 4010.

The PAP device 4000 may have an electrical power supply 4210, and one or more input devices 4220. Electrical components 4200 may be mounted on a single Printed Circuit Board Assembly (PCBA) 4202. In an alternative form, the PAP device 4000 may include more than one PCBA 4202.

8.5 GLOSSARY

For the purposes of the present technology disclosure, in certain forms of the present technology, one or more of the following definitions may apply. In other forms of the present technology, alternative definitions may apply.

8.5.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

8.5.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

8.5.3 PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g$-$f/cm^2$, hectopascal. 1 $cmH_2O$ is equal to 1 $g$-$f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ pascal (Pa), considered the threshold of human hearing.

8.5.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.5.5 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

8.5.6 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

8.5.7 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

8.6 OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

8.7 REFERENCE SIGNS LIST 100 mask system
110 mask frame
112 opening
115 exterior surface
120 patient contacting portion
130 shroud
132 opening
134 opening
140 mask vent
141 venting area
142 vent hole
150 continuous side wall
241 venting area
242 vent hole
250 side wall
341 venting area
342 vent hole
350 side wall
441 venting area
442 vent hole
445 rib
450 side wall
540 mask vent
542 vent hole
544 inlet portion
545 side wall
546 vent portion
548 outlet portion
549 interior wall
550 side wall
580 elbow assembly
581 first end
582 second end
583 collar
584 baffle
590 intake port
592 exhaust port
600 mask system
610 mask frame
617 flange
620 cushion
625 forehead support
640 vent cap
642 vent hole
643 main body
644 inlet portion
645 side wall
646 vent portion
647 support wall
647.1 wall portion
647.2 wall portion
648 outlet portion
649 interior wall
650 side wall
660 engagement ring
661 groove
662 groove
664 entry opening
680 elbow assembly
681 first end
682 second end
684 baffle
686 flange
687 annular wall
690 intake port
692 exhaust port
740 mask vent
742 vent hole
744 inlet portion
745 side wall
746 vent portion
748 outlet portion
749 interior wall
750 side wall
780 elbow assembly
781 first end
782 second end
798 air delivery tube
799 cuff
840 mask vent
842 vent hole
845 side wall
848 outlet portion
850 side wall
852 wing
880 elbow assembly
940 mask vent
942 vent hole
945 side wall
946 vent portion
948 outlet portion 949 interior wall
950 side wall
980 elbow assembly
981 first end
982 second end
983 support wall
1000 patient
1040 mask vent
1042 vent hole
1048 outlet portion
1049 vent wall
1050 side wall
1080 elbow assembly
1081 first end
1082 second end
1100 partner
1140 mask vent
1142 vent hole
1148 outlet portion
1149 vent wall
1150 side wall
1180 elbow assembly
1181 first end
1182 second end
1240 vent
1242 vent hole
1248 outlet portion
1249 vent wall
1250 side wall
1280 elbow assembly
1281 first end
3000 patient interface
3100 seal-forming structure
3110 sealing flange
3120 support flange
3200 plenum chamber
3400 vent
3600 connection port
3700 forehead support
4000 PAP device
4010 external housing
4012 upper portion
4014 portion
4015 panel
4016 chassis
4018 handle
4020 pneumatic block
4100 pneumatic component
4112 inlet air filter
4142 blower
4170 air circuit
4200 electrical component
4202 board assembly
4210 electrical power supply
4220 input device
5000 humidifier

The invention claimed is:

1. A patient interface to deliver of a flow of air at a positive pressure with respect to ambient air pressure to an entrance to the patient's airways including at least the entrance of a patient's nares to ameliorate sleep disordered breathing, the patient interface comprising:

a plenum chamber pressurizable to the positive pressure above ambient air pressure, said plenum chamber including a connection port structured to receive the flow of air at the positive pressure for breathing by a patient;

a seal-forming structure constructed and arranged to seal with a region of the patient's face surrounding the entrance to the patient's airways, the seal-forming structure having a hole therein such that the flow of air at the positive pressure is delivered to at least an entrance to the patient's nares, the seal-forming structure constructed and arranged to maintain the positive pressure in the plenum chamber throughout the patient's respiratory cycle in use; and a vent constructed and arranged to allow exhaust of gases exhaled by the patient from an interior of the plenum chamber to ambient, the vent including:

a venting area including an exterior surface, a plurality of vent holes each extending through a thickness of the venting area and each including a vent exit along the exterior surface of the venting area, wherein each of the plurality of vent holes includes a circular cross-section along its length, and wherein each of the plurality of vent holes defines an axis of exhaust vent airflow from the vent exit, a continuous side wall structured to surround the vent exits of the vent holes so as to enhance dispersion or diffusion of exhaust vent airflow from the vent exits, and a plurality of interior ribs arranged within the continuous side wall, each of the plurality of interior ribs structured and arranged to project from the exterior surface of the venting area outwards from the vent exits of the vent holes and away from the interior of the plenum chamber, wherein each of the plurality of interior ribs structured and arranged to extend from the continuous side wall and at least partially into the venting area, wherein the plurality of interior ribs are spaced around a perimeter of the continuous side wall to at least partially divide the exhaust vent airflow exiting the vent exits, wherein the continuous side wall includes a free end along its perimeter, wherein the continuous side wall is structured and arranged to project outwards from the exterior surface of the venting area and away from the interior of the plenum chamber to the free end, wherein the continuous side wall includes a height that is larger than a length of each of the plurality of vent holes, wherein the continuous side wall and the plurality of interior ribs are structured and arranged such that the exhaust vent airflow encounters the continuous side wall and the plurality of interior ribs upon exiting the vent exits of the vent holes, and wherein the continuous side wall includes a longitudinal axis, an exterior surface and an opposite interior surface, wherein a thickness of the continuous sidewall is formed by a width extending from the exterior surface to the interior surface, the plurality of interior ribs extend from the interior surface of the continuous sidewall and each rib of the plurality of interior ribs is spaced apart from one another with an end of each rib of the plurality of interior ribs being a free end and is a farthest end of the each rib of the plurality of ribs relative to the interior surface.

2. The patient interface according to claim 1, wherein the height of the side wall is uniform or constant along its perimeter.

3. The patient interface according to claim 1, wherein the side wall includes a uniform or constant thickness along its perimeter.

4. The patient interface according to claim 1, wherein the vent holes are arranged in columns.

5. The patient interface according to claim 1, wherein the side wall is structured to surround the entire venting area.

6. The patient interface according to claim 1, wherein the side wall includes a generally similar shape to the venting area.

7. The patient interface according to claim 1, wherein each vent hole includes a generally part conic shape.

8. The patient interface according to claim 1, wherein each vent hole includes a generally cylindrical shape.

9. The patient interface according to claim 1, wherein the vent is provided to a mask frame.

10. The patient interface according to claim 1, wherein the vent is provided to an elbow assembly.

11. The patient interface according to claim 10, wherein the vent is integrally formed in one piece with the elbow assembly.

12. The patient interface according to claim 10, wherein at least a portion of the vent is formed separately from the elbow assembly and attached thereto.

13. The patient interface according to claim 12, wherein the vent is a vent cap structured to attach to the elbow assembly.

14. The patient interface according to claim 12, wherein the vent holes are provided to the elbow assembly and the side wall is provided as a cover piece structured to attach to the elbow assembly.

15. The patient interface according to claim 10, wherein the elbow assembly includes a baffle that separates an intake port from an exhaust port, and the vent is provided at an outlet of the exhaust port.

16. The patient interface according to claim 1, wherein the vent is recessed within an interior of the patient interface.

17. The patient interface according to claim 1, wherein the plurality of vent holes is in a range of 20 holes to 80 holes, wherein the height of the continuous side wall is in a range of 4.5 mm to 18 mm, and wherein a ratio between the plurality of vent holes and the height of the continuous side wall is configured to reduce venting noise.

18. The patient interface according to claim 1, wherein the height of the continuous side wall is configured to reduce air velocity downstream from the vent exits of the plurality of vent holes so as to enhance dispersion or diffusion of exhaust vent flow.

19. The patient interface according to claim 18, wherein the height of the continuous side wall is configured to prevent additional air surrounding the venting area from being pulled into the exhaust vent airflow exiting the vent exits.

20. The patient interface according to claim 1, wherein the side wall is perpendicular to the exterior surface of the venting area.

21. The patient interface according to claim 1, wherein the height of the side wall is over 10 times greater than a diameter of each of the plurality of vent holes.

22. The patient interface according to claim 1, wherein the plurality of vent holes within the venting area is 36 holes and the height of the continuous side wall is 10 mm.

23. The patient interface according to claim 1, wherein the plurality of vent holes is in a range of 20 holes to 80 holes.

24. The patient interface according to claim 1, wherein the continuous side wall and each of the plurality of interior ribs are structured and arranged to project outwards from the exterior surface of the venting area in a direction of the exhaust vent airflow.

25. The patient interface according to claim 1, wherein each of the plurality of interior ribs is structured and arranged to project radially from the continuous side wall towards a center portion of the venting area.

26. A mask system to deliver of a flow of air at a positive pressure with respect to ambient air pressure to an entrance to the patient's airways including at least the entrance of a patient's nares to ameliorate sleep disordered breathing, the mask system comprising:
 a frame;
 a cushion provided to the frame and adapted to form a seal with a patient's nose and/or mouth;
 an elbow assembly provided to the frame and adapted to be connected to an air delivery tube that delivers breathable gas to the patient; and
 a mask vent including
  an interior wall extending transversely across a vent portion of the mask vent,
  a plurality of vent holes each extending through a thickness of the interior wall and each including a vent exit, wherein each of the plurality of vent holes includes a circular cross-section along its length, and wherein each of the plurality of vent holes defines an axis of exhaust vent airflow from the vent exit,
  a continuous side wall integrally formed in one piece with the interior wall and structured to surround the vent exits of the plurality of vent holes so as to enhance dispersion or diffusion of exhaust vent airflow from the vent exits, and
  a plurality of interior ribs arranged within the continuous side wall, each of the plurality of interior ribs structured and arranged to project from the interior wall and outwards from the vent exits of the vent holes in a direction of the exhaust vent airflow,
  wherein each of the plurality of interior ribs structured and arranged to extend from the continuous side wall and at least partially into the vent portion,
  wherein the plurality of interior ribs are spaced around a perimeter of the continuous side wall to at least partially divide the exhaust vent airflow exiting the vent exits, wherein
  the continuous side wall includes a free end along its perimeter, wherein the continuous side wall is structured and arranged to project outwards from the interior wall in the direction of the exhaust vent airflow to the free end, wherein
  the continuous side wall includes a height that is larger than a length of each of the plurality of vent holes, wherein
  the continuous side wall and the plurality of interior ribs are structured and arranged such that the exhaust vent airflow encounters the continuous side wall and the plurality of interior ribs upon exiting the vent exits of the vent holes, and wherein the continuous side wall includes a longitudinal axis and an interior surface that is cylindrical, the plurality of interior ribs extend from the interior surface of the continuous sidewall and each rib of the plurality of interior ribs is spaced apart from one another with an end of each rib of the plurality of interior ribs being a free end and is a farthest end of the each rib of the plurality of ribs relative to the interior surface.

27. The mask system according to claim 26, wherein the mask vent is provided to the frame.

\* \* \* \* \*